US010202585B2

(12) United States Patent
Tomer et al.

(10) Patent No.: US 10,202,585 B2
(45) Date of Patent: *Feb. 12, 2019

(54) MODIFICATION OF ENZYMATIC CROSSLINKERS FOR CONTROLLING PROPERTIES OF CROSSLINKED MATRICES

(71) Applicant: LIFEBOND, LTD., Caesarea (IL)

(72) Inventors: Guy Tomer, Modi'in (IL); Orahn Preiss-Bloom, Zichron Yakov (IL)

(73) Assignee: LIFEBOND LTD, Caesarea (IL)

(*) Notice: Subject to any disclaimer, the term of this patent is extended or adjusted under 35 U.S.C. 154(b) by 69 days.

This patent is subject to a terminal disclaimer.

(21) Appl. No.: 14/696,390

(22) Filed: Apr. 25, 2015

(65) Prior Publication Data
US 2015/0291939 A1    Oct. 15, 2015

Related U.S. Application Data

(63) Continuation of application No. 13/517,906, filed as application No. PCT/IB2010/056008 on Dec. 22, 2010, now Pat. No. 9,066,991.

(60) Provisional application No. 61/289,368, filed on Dec. 22, 2009.

(51) Int. Cl.
| C12N 9/10 | (2006.01) |
| A61L 17/08 | (2006.01) |
| A61L 24/10 | (2006.01) |
| A61K 38/45 | (2006.01) |
| A61L 24/08 | (2006.01) |
| A61L 27/20 | (2006.01) |
| A61L 27/22 | (2006.01) |
| C07K 14/78 | (2006.01) |

(52) U.S. Cl.
CPC ............ *C12N 9/1029* (2013.01); *A61L 24/08* (2013.01); *A61L 24/10* (2013.01); *A61L 27/20* (2013.01); *A61L 27/22* (2013.01); *C07K 14/78* (2013.01); *C12N 9/1044* (2013.01); *A61K 38/45* (2013.01); *A61L 17/08* (2013.01); *A61L 2400/04* (2013.01); *C12Y 203/02013* (2013.01)

(58) Field of Classification Search
None
See application file for complete search history.

(56) References Cited

U.S. PATENT DOCUMENTS

| 1,394,654 A | 10/1921 | Tressler |
| 1,844,679 A | 2/1932 | Price |
| 1,873,580 A | 8/1932 | Hailwood |
| 1,950,483 A | 5/1934 | Christopher et al. |
| 2,048,499 A | 7/1936 | Gellednien |
| 2,126,305 A | 8/1938 | Babcock |
| 2,166,074 A | 7/1939 | Reichel |
| 2,398,004 A | 5/1946 | Houck et al. |
| 2,417,713 A | 3/1947 | Stein |
| 2,558,065 A | 6/1951 | Linwood |
| 2,658,001 A | 11/1953 | Young |
| 2,719,145 A | 9/1955 | Skelton et al. |
| 2,803,548 A | 8/1957 | Hagetry |
| 3,220,845 A | 11/1965 | Lee |
| 3,600,482 A | 8/1971 | Salyer et al. |
| 3,939,001 A | 2/1976 | Clausi et al. |
| 3,988,479 A | 10/1976 | Stephan |
| 4,188,373 A | 2/1980 | Krezanoski |
| 4,188,465 A | 2/1980 | Schneider et al. |
| 4,224,348 A | 9/1980 | Hayashi |
| 4,344,181 A | 10/1982 | Baecklund |
| 4,426,443 A | 1/1984 | Shank |
| 4,478,822 A | 10/1984 | Haslam |
| 4,527,906 A | 7/1985 | Jezbera |
| 4,572,906 A | 2/1986 | Sparkes et al. |
| 4,605,513 A | 8/1986 | DiMarchi |
| 4,651,725 A | 3/1987 | Kifune |
| 4,711,848 A | 8/1987 | Insley |
| 4,729,897 A | 3/1988 | Poppe |
| 4,837,379 A | 6/1989 | Weinberg |
| 4,889,920 A | 12/1989 | Mueller |
| 4,891,319 A | 1/1990 | Roser |
| 4,931,501 A | 6/1990 | Lai et al. |

(Continued)

FOREIGN PATENT DOCUMENTS

| CA | 896965 A | 4/1972 |
| CN | 1161790 C | 8/2004 |

(Continued)

OTHER PUBLICATIONS

Nio et al. Gelation Mechanism of Protein Solution by Transglutaminase; Agricultural and Biol Chem 50(4), 1986: p. 851-855.

O'Halloran DM et al. Characterization of a microbial transglutaminase cross-linked type II collagen scaffold. Tissue Eng. Jun. 2006; 12(6): 1467-74.

Ohtake Y et al. Transglutaminase catalyzed dissociation and association of protein-polyamine complex; Life Sciences 2007; 81 ,7: p. 577-584.

Otani Y et al. Sealing Effect of Rapidly Curable Gelatin-Poly (L-Glutamic Acid) Hydrogel Glue on Lung Air Leak; Ann Thorac Surg 1999, 67, 922-6.

Rodriguez et al. Combined effect of plasticizers and surfactants on the physical properties of starch based edible films; Food Research International 39 (2006) 840-6.

(Continued)

*Primary Examiner* — Robert J Yamasaki
*Assistant Examiner* — Charles Zoltan Constantine
(74) *Attorney, Agent, or Firm* — Graeser Associates International Inc; Dvorah Graeser

(57) ABSTRACT

Improved matrix or hydrogel that is formed by enzymatic crosslinking of polymers wherein the crosslinking enzyme molecules have been modified for the purpose of improving the crosslinking density, mechanical properties, or other properties of the matrix, and/or to provide improved control over the rate and/or extent of crosslinking, wherein the enzyme molecules are modified to alter the perceived volume of the enzyme molecules in the crosslinked matrix being formed. Methods of production and of use are also provided.

35 Claims, 12 Drawing Sheets

(56) References Cited

U.S. PATENT DOCUMENTS

| | | |
|---|---|---|
| 4,948,540 A | 8/1990 | Nigam |
| 4,952,618 A | 8/1990 | Olsen |
| 4,971,954 A | 11/1990 | Brodsky |
| 4,985,250 A | 1/1991 | Bee et al. |
| 5,015,677 A | 5/1991 | Benedict et al. |
| 5,026,785 A | 6/1991 | Mage |
| 5,059,636 A | 10/1991 | Grenga |
| 5,147,344 A | 9/1992 | Sachau |
| 5,209,776 A | 5/1993 | Bass et al. |
| 5,399,361 A | 3/1995 | Song |
| 5,428,014 A | 6/1995 | Labroo et al. |
| 5,433,943 A | 7/1995 | Osipow |
| 5,441,193 A | 8/1995 | Gravener |
| 5,480,644 A | 1/1996 | Freed |
| 5,487,889 A | 1/1996 | Eckert et al. |
| 5,487,895 A | 1/1996 | Dapper |
| 5,490,984 A | 2/1996 | Freed |
| 5,503,638 A | 4/1996 | Cooper et al. |
| 5,508,202 A | 4/1996 | Enomoto |
| 5,525,335 A | 6/1996 | Kitahara et al. |
| 5,549,628 A | 8/1996 | Cooper et al. |
| 5,549,904 A | 8/1996 | Juergensen |
| 5,575,803 A | 11/1996 | Cooper et al. |
| 5,618,312 A | 3/1997 | Yui |
| 5,702,409 A | 12/1997 | Rayburn et al. |
| 5,736,132 A | 4/1998 | Juergensen et al. |
| 5,752,965 A | 5/1998 | Francis et al. |
| 5,752,974 A | 5/1998 | Rhee et al. |
| 5,810,855 A | 9/1998 | Rayburn et al. |
| 5,834,232 A | 11/1998 | Bishop et al. |
| 5,895,412 A | 4/1999 | Tucker |
| 5,939,385 A | 8/1999 | Labroo et al. |
| 5,931,165 A | 9/1999 | Reich et al. |
| 5,948,662 A | 9/1999 | Kobayashi et al. |
| 6,007,613 A | 12/1999 | Izoret |
| 6,030,821 A | 2/2000 | Soeda |
| 6,046,024 A | 4/2000 | Burton |
| 6,047,861 A | 4/2000 | Vidal |
| 6,054,122 A | 4/2000 | MacPhee et al. |
| 6,063,061 A | 5/2000 | Wallace et al. |
| 6,066,325 A | 5/2000 | Wallace |
| 6,083,524 A | 7/2000 | Sawhney |
| 6,100,053 A | 8/2000 | Bech et al. |
| 6,107,401 A | 8/2000 | Dado et al. |
| 6,117,425 A | 9/2000 | MacPhee et al. |
| 6,121,013 A | 9/2000 | Yamaguchi |
| 6,132,759 A | 10/2000 | Schacht et al. |
| 6,136,341 A | 10/2000 | Petito et al. |
| 6,156,330 A | 12/2000 | Tsukada |
| 6,162,241 A | 12/2000 | Coury et al. |
| 6,190,896 B1 | 2/2001 | Fraij |
| 6,197,325 B1 | 3/2001 | MacPhee et al. |
| 6,228,393 B1 | 5/2001 | DiCosmo |
| 6,267,957 B1 | 7/2001 | Green et al. |
| 6,303,752 B1 * | 10/2001 | Olsen .................... A21D 2/26 435/189 |
| 6,420,148 B2 | 1/2002 | Yamaguchi |
| 6,371,975 B2 | 4/2002 | Cruise et al. |
| 6,413,742 B1 | 7/2002 | Olsen et al. |
| 6,454,787 B1 | 9/2002 | Maddalo |
| 6,458,386 B1 | 10/2002 | Schacht |
| 6,461,849 B1 | 10/2002 | Olsen |
| 6,465,001 B1 | 10/2002 | Hubbell |
| 6,475,516 B2 | 11/2002 | DiCosmo |
| 6,509,039 B1 | 1/2003 | Nies |
| 6,527,751 B2 | 3/2003 | Fischer et al. |
| 6,531,147 B2 | 3/2003 | Sawhney |
| 6,544,227 B2 | 4/2003 | Sahatjian et al. |
| 6,559,119 B1 | 5/2003 | Burgess et al. |
| 6,576,685 B2 | 6/2003 | Stedronsky |
| 6,605,066 B1 | 8/2003 | Gravagna et al. |
| 6,610,043 B1 | 8/2003 | Ingenito |
| 6,649,386 B2 | 11/2003 | Roser |
| 6,656,193 B2 | 12/2003 | Grant et al. |
| 6,663,594 B2 | 12/2003 | Sahatjian |
| 6,682,760 B2 | 1/2004 | Noff |
| 6,704,210 B1 | 3/2004 | Myers |
| 6,706,690 B2 | 3/2004 | Reich |
| 6,762,336 B1 | 7/2004 | MacPhee et al. |
| 6,773,156 B2 | 8/2004 | Henning |
| 6,833,258 B2 | 12/2004 | Yokoyama et al. |
| 6,863,783 B2 | 3/2005 | Lin |
| 6,875,796 B2 | 4/2005 | Stedronsky |
| 6,939,358 B2 | 9/2005 | Palacios et al. |
| 6,992,172 B1 | 2/2006 | Chang et al. |
| 7,019,191 B2 | 3/2006 | Looney et al. |
| 7,045,601 B2 | 5/2006 | Metzner |
| 7,074,981 B2 | 7/2006 | Chalmers |
| 7,108,876 B2 | 9/2006 | Grindstaff |
| 7,109,163 B2 | 9/2006 | Pendharkar |
| 7,129,210 B2 | 10/2006 | Lowinger |
| 7,186,684 B2 | 3/2007 | Pendharkar |
| 7,189,410 B1 | 3/2007 | Drohan et al. |
| 7,196,054 B1 | 3/2007 | Drohan et al. |
| 7,208,171 B2 | 4/2007 | Messersmith |
| 7,208,179 B1 | 4/2007 | Drohan et al. |
| 7,220,836 B2 | 5/2007 | Roser |
| 7,229,959 B1 | 6/2007 | Drohan et al. |
| 7,241,730 B2 | 7/2007 | Hubbell |
| 7,285,580 B2 | 10/2007 | Stedronsky |
| 7,320,962 B2 | 1/2008 | Reich |
| 7,435,425 B2 | 10/2008 | Qian |
| 7,459,425 B2 | 12/2008 | Wan et al. |
| 7,468,350 B2 | 12/2008 | Gong |
| 7,766,891 B2 | 8/2010 | McGurk |
| 7,998,466 B2 | 8/2011 | Hadba |
| 8,133,484 B2 | 3/2012 | Preiss-Bloom et al. |
| 8,367,388 B2 | 2/2013 | Bloom et al. |
| 8,475,812 B2 | 7/2013 | Nur |
| 8,722,039 B2 | 5/2014 | Preiss-Bloom |
| 9,066,991 B2 | 6/2015 | Preiss-Bloom |
| 9,297,464 B1 | 3/2016 | Wang |
| 2001/0018598 A1 | 8/2001 | Cruise |
| 2002/0015724 A1 | 2/2002 | Yang |
| 2003/0008831 A1 | 1/2003 | Yang |
| 2003/0022832 A1 | 1/2003 | Montero Garcia |
| 2003/0035786 A1 | 2/2003 | Hendriks |
| 2003/0120284 A1 | 6/2003 | Palacios et al. |
| 2003/0135238 A1 | 7/2003 | Milbocker |
| 2003/0219857 A1 | 11/2003 | Chou |
| 2003/0232944 A1 | 12/2003 | Molenberg |
| 2004/0093029 A1 | 5/2004 | Zubik et al. |
| 2004/0106344 A1 | 6/2004 | Looney |
| 2004/0131728 A1 | 7/2004 | Ootsuka |
| 2005/0113937 A1 | 5/2005 | Binette et al. |
| 2005/0129733 A1 | 6/2005 | Milbocker |
| 2005/0147646 A1 | 7/2005 | Nilsson |
| 2005/0209441 A1 | 9/2005 | Lile |
| 2005/0238683 A1 | 10/2005 | Adhikari et al. |
| 2005/0249839 A1 | 11/2005 | Ishida |
| 2005/0271727 A1 | 12/2005 | Yao |
| 2006/0078962 A1 | 4/2006 | Chen et al. |
| 2006/0100138 A1 | 5/2006 | Olsen |
| 2006/0155234 A1 | 7/2006 | MacPhee et al. |
| 2006/0002585 A1 | 11/2006 | Yang et al. |
| 2006/0258560 A1 | 11/2006 | Yang et al. |
| 2006/0269590 A1 | 11/2006 | Trotter |
| 2007/0021703 A1 | 1/2007 | McCarthy |
| 2007/0082023 A1 | 4/2007 | Hopman et al. |
| 2007/0128152 A1 | 6/2007 | Hadba |
| 2007/0172432 A1 | 7/2007 | Stopek |
| 2007/0246505 A1 | 10/2007 | Pace-Florida et al. |
| 2008/0161757 A1 | 7/2008 | Nayak |
| 2008/0187591 A1 | 8/2008 | Rhee et al. |
| 2008/0195037 A1 | 8/2008 | Hissong |
| 2008/0213243 A1 * | 9/2008 | Preiss-Bloom ........ A61K 38/39 424/94.63 |
| 2008/0260801 A1 | 10/2008 | Ahlers |
| 2008/0286376 A1 | 11/2008 | Qian et al. |
| 2009/0175946 A1 | 7/2009 | Gaissmaier et al. |
| 2009/0191269 A1 | 7/2009 | Gaissmaier |
| 2010/0008989 A1 | 1/2010 | Attar |
| 2010/0063459 A1 | 3/2010 | Preiss-Bloom |

(56) References Cited

U.S. PATENT DOCUMENTS

| | | | |
|---|---|---|---|
| 2011/0021964 A1 | 1/2011 | Larsen | |
| 2012/0209319 A1 | 8/2012 | Bianco-Peled | |
| 2012/0226211 A1 | 9/2012 | Preiss-Bloom | |

FOREIGN PATENT DOCUMENTS

| | | |
|---|---|---|
| CN | 1617735 A | 5/2005 |
| CN | 1646029 A | 7/2005 |
| DE | 102005054940 A1 | 5/2007 |
| DE | 102006033168 A1 | 1/2008 |
| EP | 0073908 A1 | 3/1983 |
| EP | 0302953 | 2/1989 |
| EP | 0707474 | 4/1996 |
| EP | 0726317 | 8/1996 |
| EP | 0745670 | 12/1996 |
| EP | 0777726 | 6/1997 |
| EP | 0815742 | 1/1998 |
| EP | 0871712 | 10/1998 |
| EP | 0876166 | 11/1998 |
| EP | 0927053 | 7/1999 |
| EP | 0947142 | 10/1999 |
| EP | 0982038 | 3/2000 |
| EP | 1073342 A1 | 2/2001 |
| EP | 1124590 | 8/2001 |
| EP | 1263327 | 12/2002 |
| EP | 1267826 | 1/2003 |
| EP | 1267876 | 1/2003 |
| EP | 1288264 | 3/2003 |
| EP | 1372492 | 1/2004 |
| EP | 1494730 | 1/2005 |
| EP | 20030744835 | 1/2005 |
| EP | 1574229 | 9/2005 |
| EP | 1857494 | 11/2007 |
| EP | 1948260 | 7/2008 |
| EP | 2133069 | 12/2009 |
| JP | 2204407 | 8/1990 |
| JP | 2255888 | 10/1990 |
| JP | H0395109 A | 4/1991 |
| JP | 7328108 | 12/1995 |
| JP | 10510183 | 10/1998 |
| JP | 2002515300 A | 5/2002 |
| JP | 2004283371 A | 10/2004 |
| JP | 2004531534 A | 10/2004 |
| JP | 2005152653 A | 6/2005 |
| JP | 2006503612 A | 2/2006 |
| JP | 07227228 | 9/2007 |
| JP | 2007537314 A | 12/2007 |
| JP | 2009542384 A | 12/2009 |
| JP | 2010521994 A | 7/2010 |
| WO | 9320837 A1 | 10/1993 |
| WO | 9617929 | 5/1996 |
| WO | WO1996017929 | 6/1996 |
| WO | 9640791 | 12/1996 |
| WO | WO1996040791 | 12/1996 |
| WO | 9710701 | 3/1997 |
| WO | 9722372 | 6/1997 |
| WO | WO1997022372 | 6/1997 |
| WO | 9728834 A1 | 8/1997 |
| WO | 9729715 A1 | 8/1997 |
| WO | 9729715 A2 | 8/1997 |
| WO | WO199729715 | 8/1997 |
| WO | 9737694 A1 | 10/1997 |
| WO | WO199741899 | 11/1997 |
| WO | WO1997040701 | 11/1997 |
| WO | 9835026 | 8/1998 |
| WO | WO/1998/035026 | 8/1998 |
| WO | 99010952 | 3/1999 |
| WO | 9957254 A1 | 11/1999 |
| WO | WO/2000/022103 | 4/2000 |
| WO | WO/2000/076533 | 12/2000 |
| WO | 0115750 | 3/2001 |
| WO | WO/2001/015750 | 3/2001 |
| WO | 02085422 | 10/2002 |
| WO | 02098937 A2 | 12/2002 |
| WO | 0311352 | 2/2003 |
| WO | WO/2003/011352 | 2/2003 |
| WO | 0372155 | 9/2003 |
| WO | WO/2003/072155 | 9/2003 |
| WO | WO/2003/072157 | 9/2003 |
| WO | WO2003074004 | 9/2003 |
| WO | WO2003080144 | 10/2003 |
| WO | WO2003086493 | 10/2003 |
| WO | WO2004004875 | 1/2004 |
| WO | WO/2004/014969 | 2/2004 |
| WO | 20040024195 A1 | 3/2004 |
| WO | WO/2004/029096 | 4/2004 |
| WO | WO2004028404 | 4/2004 |
| WO | WO/2004/098671 | 11/2004 |
| WO | WO/2004/105485 | 12/2004 |
| WO | 2005006991 A2 | 1/2005 |
| WO | 2005016170 A2 | 2/2005 |
| WO | WO/2005/061701 | 7/2005 |
| WO | 2005092204 A2 | 10/2005 |
| WO | WO/2006/014567 | 2/2006 |
| WO | WO/2006/014568 | 2/2006 |
| WO | WO2006016809 | 2/2006 |
| WO | WO2006027622 | 3/2006 |
| WO | WO2006056700 | 6/2006 |
| WO | 2006086479 A1 | 8/2006 |
| WO | WO/2006/134148 | 12/2006 |
| WO | WO2006128685 | 12/2006 |
| WO | 200800655 | 1/2007 |
| WO | 2007008229 | 1/2007 |
| WO | WO/2008/006545 | 1/2007 |
| WO | 20070057175 A2 | 5/2007 |
| WO | WO2007057175 | 5/2007 |
| WO | WO/2007/122232 | 11/2007 |
| WO | WO/2007/123350 | 11/2007 |
| WO | WO/2007/126411 | 11/2007 |
| WO | WO/2007/134118 | 11/2007 |
| WO | WO2008006544 | 1/2008 |
| WO | WO2008006545 | 1/2008 |
| WO | WO/2008/016983 | 2/2008 |
| WO | 07025726 A1 | 6/2008 |
| WO | 20080076407 A2 | 6/2008 |
| WO | WO/2008/073938 | 6/2008 |
| WO | WO2008076407 | 6/2008 |
| WO | 2008103981 | 8/2008 |
| WO | WO/2008/103891 | 8/2008 |
| WO | WO/2009/012882 | 1/2009 |
| WO | WO/2009/026158 | 2/2009 |
| WO | WO/2009/036014 | 3/2009 |
| WO | 2009075329 A1 | 6/2009 |
| WO | WO/2009/073193 | 6/2009 |
| WO | WO/2009/105614 | 8/2009 |
| WO | 2009153750 A2 | 12/2009 |
| WO | 2009153751 A2 | 12/2009 |
| WO | 20090153748 A2 | 12/2009 |
| WO | WO/2010/027471 | 3/2010 |
| WO | 2010145817 A2 | 12/2010 |
| WO | 2011077388 A1 | 6/2011 |
| WO | 2011079336 A1 | 7/2011 |

OTHER PUBLICATIONS

Sanborn TJ et al. In situ crosslinking of a biomimetic peptide-PEGhydrogel via thermally triggered activation of factor XIII; Biomaterials 2002, 23, 2703-10.

Serafinie-Fracassini D et al. First Evidence for Polyamine Conjugation Mediated by an Enzymic Activity in Plants; Plant Physiol. (1988) 87, 757-761.

Shojaei AM et al. Mechanisms of buccal mucoadhesion of novel copolymers of acrylic acid and polyethylene glycol monomethylether monomethacrylate; Journal of Control Release, 1997, 47, 151-61. 27.

Silva EA et al. Spatiotemporal control of vascular endothelial growth factor delivery from injectable hydrogels enhances angiogenesis; J Thromb Haemost 2007, 5, 590-8.

Silverman HG et al. Understanding Marine Mussel Adhesion; Mar Biotechnol (NY) 2007, 9, 661-81.

Sperinde J et al. Control and Prediction of Gelation Kinetics in Enzymatically Cross-Linked Poly(ethylene glycol) Hydrogels; Macromolecules 2000, 33, 5476-5480.

(56) References Cited

OTHER PUBLICATIONS

Strausberg RL et al, Protein-based medical adhesives, Trends Biotechnol 1990;8:53-5.

Sung HW et al. Evaluation of gelatin hydrogel crosslinked with various crosslinking agents as bioadhesives: In vitro study; J Biomed Mater Res 1999, 46, 520-30.

Ulijn RV et al. Designing peptide based nanomatenals; Chem Soc Rev 2008, 37, 664-75.

Hideraka Nagatomo, Gelatin-based adhesive has fibrin sealant benefit without use of blood products. Biosci, Biotechnol. Biochem, 2005, 128-136, 69 (1).

Blood Weekly Editors. Gelatin-based adhesive has fibrin sealant benefit without use of blood products, Copyright 2004, Blood Weekly via NewsRx.com.

Office Action for EP patent application 07867783.8 dated Aug. 28, 2011.

Cui L, et al. Purification and characterization of transglutaminase from a newly isolated Streptomyces hygroscopicus. 2007: 105(2). p. 612-618.

D'Cruz NM, et al. Thermal Unfolding of Gelatin in Solids as Affected by the Glass Transition, J Food Science 2005: 70 (2), Kozlov PV, Burdygina GI.

Search Report for EP patent application 09162590.5 dated Sep. 2, 2009.

Bello J, et al. Mechanism of Gelation of Gelatin. Influence of Certain Electrolytes on the Melting Points of Gels of Gelatin and Chemically Modified Gelatins. Am Chem Soc. Sep. 1956 (60). p. 1299-1306.

Crowe LM,et al. Is Trehalose Special for Preserving Dry Biomaterials? Biophysical Journal 1996 (71): 2087-2091.

Norie N, et al. Factors Affecting the Gelation of a Gelatin Solution in the Presence of Sugar. Journal of Home Economics of Japan. 55(2): p. 159-166 (2004).

J.M. Rocko et al. (1982). J. Trauma 22:635.

OA for EP patent application 09162590.5 dated: Jul. 6, 2010.

D.B. Kendrick, Blood Program in WW II ( Washington, DC: Office of the Surgeon General, Department of Army; 1989), 363-368.

Gorman, J.J; J Bio. Chem. 1980, 255, 419-427.

Kahlem, P.; Acad. Sci U.S.A. 1996, 93, 14580-14585.

Etoh, Y.; Biochem, Biophys. Res Commun. 1986, 136, 51-56.

Hohenadi, C.; J. Biol. Chem. 1955, 270, 23415-23420.

Gross, M.; J. Biol. Chem. 1975, 250, 4648-4655.

Groenen, P.; Eur. J. Biochem. 1994, 220, 795-799.

Grootjans, J. J. Biol. Chem. 1995, 270, 22855-22858.

Owen et al. N. Engl. J. Med. 309:694-698, 1983.

OA for IL patent application 199357 dated: Mar. 20, 2011.

IUB Nomenclature Committee. "Units of enzyme activity. Recommendations 1978. Prepared by Karlson P, Bielka H, Horecker BL, Jakoby WB, Keil B, Liébecq C, et al." Eur J Biochem 97 (1979): 319-20.

Nemes, Zoltan, Lyuben N. Marekov, and Peter M. Steinert. "Involucrin Cross-linking by transglutaminase 1 Binding to Membranes Directs Residue Specificity." Journal of Biological Chemistry 274.16 (1999): 11013-11021.

Rubin, Andrew L., and Robert H. Rice. "Differential regulation by retinoic acid and calcium of transglutaminases in cultured neoplastic and normal human keratinocytes." Cancer research 46.5 (1986): 2356-2361.

Pasternack, Ralf, et al. "A fluorescent substrate of transglutaminase for detection and characterization of glutamine acceptor compounds." Analytical biochemistry 249.1 (1997): 54-60.

Johnson, Gail VW, et al. "Transglutaminase activity is increased in Alzheimer's disease brain." Brain research 751.2 (1997): 323-329.

Lichtenauer, Michael, et al. "Phosphate buffered saline containing calcium and magnesium elicits increased secretion of interleukin-1 receptor antagonist." Laboratory Medicine 40.5 (2009): 290-293.

D'Argenio, G., et al. "Differential expression of multiple transglutaminases in human colon: impaired keratinocyte transglutaminase expression in ulcerative colitis." Gut 54.4 (2005): 496-502.

McDermott, Martin K., et al. "Mechanical properties of biomimetic tissue adhesive based on the microbial transglutaminase-catalyzed crosslinking of gelatin." Biomacromolecules 5.4 (2004): 1270-1279.

"Kei-ichi Yokoyama et al., ""In vitro refolding process of urea-denatured microbialtransglutaminase without pro-peptide sequence,"" Protein Expression and Purificationvol. 26 (2002): 329-335."

"K. V. Rajagopalan et al., ""Competitive Inhibition of Enzyme Activity by Urea,"" TheJournal of Biological Chemistry vol. 236, No. 4 (Apr. 1961 ): 1 059-1065."

"Aurin M. Chase, Hildegard C. von Meier and Vincent J. Menna, ""New CompetitiveInhibition and Irreversible Inactivation of Yeast Invertase by Urea,"" Journal of Cellularand Comparative Physiology vol. 59, Issue 1 (1962): 1, accessed Jun. 22, 2016,doi: 10.1 002/jcp.1 030590102."

"Pauline M. Emerson and J. H. Wilkinson, ""Urea and oxalate inhibition of the serumlactate dehydrogenase,"" J Clin Pathol18 (1965) 803-807, accessed Jun. 21, 2016,doi: 1 0.1136/jcp.18.6.803."

"Seikoh Horiuchi, Masayasu Inoue and Yoshimasa Morino, ""Latent Active Site in RatKidneyγ-Giutamyl Transpeptidase: Refolding Process of the Large Subunit andCharacterization of the Renatured Enzyme,"" Eur. J. Biochem. 105 (1980): 93-102."

"Anders Peter et al., ""Semenogelin I and semenogelin II, the major gel-formingproteins in human semen, are substrates for transglutaminase,"" Eur. J. Biochem. 252(1998): 216-221."

"Martin L. Schwartz et al., ""The Effect of Fibrin-Stabilizing Factor on the SubunitStructure of Human Fibrin,"" The Journal of Clinical Investigation 50 (1971 ): 1506-1513, accessed Jun. 24, 2016, doi: 1 0.1172/JCI1 06636".

"Susan M. Dallabrida, Lisa A. Falls and David H. Farrell, ""Factor XII Ia supportsmicrovascular endothelial cell adhesion and inhibits capillary tube formation in fibrin,"" Blood Journal vol. 95, No. 8 (2000): 2586-2592."

"Charles S. Greenberg, Joseph V. Dobson and Charles C. Miraglia, ""Regulation ofPlasma Factor XIII Binding to Fibrin In Vitro,"" Blood Journal vol. 66, No. 5 (1985):1028-1034."

"Michitaka Naito, Hideki Nomura and Akihisa Iguchi, ""Migration of Cultured VascularSmooth Muscle Cells into Non-Crosslinked Fibrin Gels,"" Thrombosis Research vol. 84, No. 2 (1996): 129-136".

"Eiji Niwa et al., ""Contribution of SS Bonds to the Elasticity of Actomyosin Gel in whichCoexisting Transglutaminase was inactivated,"" Fisheries Science vol. 61, No. 3(1995): 438-440".

"Hiroshi Umakoshi et al., ""Characterization of Surface Properties of MicrobialTransglutaminase Using Aqueous Two-Phase Partitioning Method,"" SolventExtraction Research and Development, Japan vol. 15 (2008): 111-115".

"J. E. Folk and P. W. Cole, ""Identification of a Functional Cysteine Essential for theActivity of Guinea Pig Liver Transglutaminase,"" J. Bioi. Chem. vol. 241, No. 13(1966): 3238-3240."

"Kei-ichi Yokoyama et al., ""Structure of Folding Intermediates at ph 4.0 and NativeState of Microbial Transglutaminase,"" Bioscience, Biotechnology, and Biochemistryvol. 67, No. 2 (2003): 291-294".

Fernandez-Diaz, M. D., P. Montero, and M. C. Gomez-Guillen. "Gel properties of collagens from skins of cod (*Gadus morhua*) and hake (*Merluccius merluccius*) and their modification by the coenhancers magnesium sulphate, glycerol and transglutaminase." Food Chemistry 74.2 (2001): 161-167.

Kozlov, P. V., and G. I. Burdygina. "The structure and properties of solid gelatin and the principles of their modification." Polymer 24.6 (1983): 651-666.

Nomura, Yoshihiro, et al. "The physicochemical property of shark type I collagen gel and membrane." Journal of agricultural and food chemistry 48.6 (2000): 2028-2032.

Otani, Yuto, Yasuhiko Tabata, and Yoshito Ikada. "Effect of additives on gelation and tissue adhesion of gelatin-poly(L-glutamic acid) mixture." Biomaterials 19.23 (1998): 2167-2173.

Totosaus, Alfonso, et al. "A review of physical and chemical protein-gel induction." International journal of food science & technology 37.6 (2002): 589-601.

(56) References Cited

OTHER PUBLICATIONS

Akira et al, Activity and Stability of Microbial Transglutaminase Modified with a Water-Soluble Polymer, JapaneseJournal of Polymer Science and Technology (Kobunshi Ronbunshu), vol. 58, No. 2, pp. 73-77 (Feb. 2001).
Office action issued for corresponding European Application No. 11192607.7, dated May 10, 2012.
Kozlov P V et al: "The structure and properties of solid gelatin and the principles of thier modification" Jun. 1, 1983 (Jun. 1, 1983), Polymer, Elsevier Science Publishers B.V, GB, pp. 651-666.
Notice of Opposition for corresponding EP application 07867783.8, dated Dec. 3, 2013.
Office action issued for corresponding European Application No. 11192607.7, dated Jan. 2, 2013.
Office action issued for related EP 11768111.4 dated Feb. 27, 2014.
Translation of office action from corresponding Japanese application No. 2009-541417, dated Dec. 3, 2013.
Translation of summary of office action from corresponding Chinese application No. CN 201080057151.0. dated Nov. 2013.
William D. Spotnitz, M.D. Commercial fibrin sealants in surgical care. The American Journal of Surgery (2001),8S-14S, 182.
Xie Z-P et al: "A novel casting forming for cermics by gelatine and enzyme catalysis" Mar. 1, 2000 (200-03-01), Journal of the European Ceramic Society, Elsevier Science Publishers, Barking, Essex, GB, pp. 253-257, XP004185604.
Office action issued for corresponding Japanese Application No. 2011-267107, dated Feb. 4, 2014—Translation.
Office action issued for related Chinese Application 201180044965.5 dated Feb. 7, 2014—Translation.
Office action issued for related Chinese Application 201180044965.5 dated Feb. 7, 2014.
De Carvalho & Grosso, "Characterization of gelatin based films modified with transglutaminase, glyoxal and formaldehyde", Food Hydrocolloids 18 (2004) 717-726.
Dong et al., ""Optimization of cross-linking parameters during production of transglutaminase-hardened spherical multinuclearmicrocapsules by complex coacervation"" Colloids and Surfaces B: Biointerfaces 63 (2008) 41-47.
Office Action of related JP2013265507 dated Jan. 20, 2015.
International Search Report for PCT/IB2009/052600.
International Search Report for PCT/IB2009/052605.
International Search Report for PCT/IB2009/052607.
EP Application 09766288.6 Office Action dated Jun. 6, 2012.
Acheson EM, Kheirabadi BS, Deguzman R, Dick EJ, Holcomb JB. Journal of Trauma-Injury Infection and Critical Care 2005, 59, 865-874.
Balakrishnan et al. (2005). Biomaterials. 26(32):6335-42.
Bertoni F et al. Transglutaminase reactivity with gelatine: perspective applications in tissue engineering; Biotechnol Lett (2006) 28:697-702.
Broderick EP, J Biomed Mater Res B Appl Biomater. Jan. 15, 2005;72(1):37-42.
Chen et al, "Enzyme-catalyzed gel formation of gelatin and chitosan: potential for in situ applications", Biomaterials vol. 24 (2003) pp. 2831-2841.
Chen et al., Biomacromolecules. 2003; 4 (6):1558-63.
Crescenzi et al, Biomacromolecules 2002, 3, 1384-1391.
Folk JE, Cole PW. Transglutaminase: mechanistic features of the active site as determined by kinetic and inhibitor studies. Biochim Biophys Acta. 1966; 122:244-64.
Garza J. L. et al. (1990). J. Trauma. 30:512-513.
Haug IJ, Draget KI, Smidsørd O. (2004). Food Hydrocolloids. 18:203-213.
Holcomb, J. B., et al. (1997). Surgical Clinics of North America. 77:943-952).
Ito A, J Biosci & Bioeng. 2003; 95(2): 196-99.
Jackson, M., et al. (1996). J. of Surg. Res. 60:15-22.
Jackson, M., et al. (1997). Surg. Forum. XL, VIII:770-772.
Jakob H. et al. (1984). J. Vasc. Surg. 1:171-180.
Japanese Application 2011-514184 Office Action.

Kheirabadi BS et al. Journal of Trauma-Injury Infection and Critical Care 2005, 59, 25-34.
Kram H. B. et al. (1990). J. Trauma. 30:97-101.
Matthew T. L. et al. (1990). Ann. Thorac. Surg. 50:40-44.
McDermott et al, "Mechanical Properties of Biomimetic Tissue Adhesive Based on the Microbial Transglutaminase-Catalyzed Crosslinking of Gelatin", Biomacromolecules 2004, vol. 5, pp. 1270-1279.
Tucci MG. (2001). J. Bioactive & Comp. Polymers. 16(2): 145-157.
Nomura et al, "Improvement of Shark Type I Collagen with Microbial Transglutaminase in Urea", Biosci. Biotech. Biochem, vol. 65, 2001, pp. 982-985.
Ochsner M. G. et al. (1990). J. Trauma. 30:884-887.
Office action for corresponding EP application 07867783.8, dated Feb. 9, 2011.
Olsen et al, Deliv Rev. Nov. 28, 2003;55(12):1547-67.
Otani et al, "Effect of additives on gelation and tissue adhesion of gelatin D-poly(L-glutamic acid) mixture", Biomaterials vol. 19 (1998) pp. 2167 to 2173.
Pusateri AE, Holcomb JB, Kheirabadi BS, Alam HB, Wade CE, Ryan KL. Journal of Trauma-Injury Infection and Critical Care 2006, 60, 674-682.
Pusateri, 2004 J Biomed Mater Res B, 15; 70(1): 114-121.
Lerner R. et al. (1990). J. Surg. Res. 48:165-181.
Sabel M. et al. (2004). Eur. Spine J. 13 (1):S97-101.
Spotnitz WD. Am J Surg 2001, 182, 8S-14S.
Weaver F. et al. (2002). Ann. Vasc. Surg. 16(3):286-93.
Werten MWT, et al. (2001). Protein Engineering. 14 (6): 447-454.
PCT Search Report for corresponding PCT application PCT/US2007/025726, dated Dec. 14, 2009.
Yokoyama K et al. Protein Exp & Purif 26, 2002: p. 329-335 2002.
Rajagopalan et al. J Biologica Chem 236(4), 1961.
Examination Report for EP2133069 dated Apr. 4, 2013.
Biomacromolecules, 2004, vol. 5, No. 4, p. 1270-1279.
De Carvalhoet al,; 1997; Physical gelation under shear for gelatin gels. Rheologica Acta 36(6): 591-609.
Examination Report for EP2303344 dated Jun. 11, 2013.
Examination Report for EP2515957 dated Jun. 24, 2013.
Extended Search report for EP2586467 dated Jun. 17, 2013.
Journal of Biomedical Materials Research. Part B, Applied Biomaterials., 2006, 5, vol. 77, No. 2, p. 416-422.
Kwon, j. 2010; Rheological Behaviour of Gelatin at High Shear Rates. Ph.D Dissertation—University of Florida pp. 1-100. specif. pp. 27-28, 46.
Office Action for CA 2,728,187 dated Apr. 2, 2013.
Office Action for JP 2011-525128 dated Aug. 6, 2013.
Orthodontics and Craniofacial Research, 2005, vol. 8, No. 3, p. 145-149.
Viscosity. Encyclopedia entry (online). Wikipedia, the free encyclopedia. "Dynamic Viscosity", p. 6 line 10; "Liquids", p. 9 line 7-8 [URL: http://en.wikipedia.org/wiki/viscosity]; no date specified.
Search report issued for corresponding PCT Application No. PCT/IB2011/053505, dated Mar. 9, 2012.
Search report issued for corresponding PCT Application No. PCT/IB2011/051714, dated Nov. 30, 2011.
Drury et al, "Hydrogels for tissue engineering: scaffold design variables and applications", Biomaterials, vol. 24, Nov. 2003, pp. 4337-4351.
Search report issued for corresponding PCT Application No. PCT/IB2010/056008, dated Apr. 19, 2011.
Office action issued for corresponding European Application No. 12155067, dated Jul. 3, 2012.
Wichman et al, "Kinetics of Refolding of Completely Reduced Human-Serum Albumin", European Journal of Biochemistry, vol. 79, 1977, pp. 339-344.
Office action issued for corresponding European Application No. 9766288.6, dated Jun. 6, 2012.
Office action issued for corresponding European Application No. 9766287.8, dated Mar. 12, 2013.
Office action issued for corresponding Chinese Application No. 200980131973.6, dated Sep. 24, 2012.
Office action issued for corresponding European Application No. 7867783.8, dated Jun. 27, 2012.

(56) References Cited

OTHER PUBLICATIONS

Office action issued for corresponding Japanese Application No. 2009-541417, dated Jan. 8, 2013.
Office action issued for corresponding Australian Application No. 2007334394, dated Jan. 4, 2013.
Office action issued for corresponding Canadian Application No. 2672651, dated Feb. 1, 2013.
Office action issued for corresponding Chinese Application No. 200780051215.4, dated Aug. 31, 2012.
Office action issued for corresponding European Application No. 12187110, dated Nov. 21, 2012.
Examination report for corresponding Australian Application No. 2007334394, dated Jul. 20, 2012.
Fernandez-Diaz, M.D. et al., "Gel Properties of Collagens from Skins of Cod (*Gadus morhua*) and Hake (*Merluccius merluccius*) and Their Modification by the Coenhancers Magnesium sulphate, Glycerol and Transglutaminase", Food Chemistry, 2001, vol. 74, pp. 161-167.
Abrams GW et al. The incidence of corneal abnormalities in the Silicone Study. Silicone Study Report 7. Arch Ophthalmol 1995;113:764-769.
Alio JL et al. A new acrylic tissue adhesive for conjunctival surgery: experimental study. Ophthalmic Res 2003, 35:306-312.
Bloom JN et al. A Light-activated surgical adhesive for sutureless ophthalmic surgery, Arch Ophthamol 2003; 121: 1591-1595.
Cooper et al. J. Thorac. Cardiovasc. Surg. 109106-116, 1995.
Cooper et al. J. Thorac. Cardiovasc. Surg. 1121319-1329, 1996.
Eidt et al. Am J Surg 1999:178:511-516.
Ghazi NG et al. Pathology and pathogenesis of retinal detachment. Eye 2002;16:411-421.
Grotenhuis Andre J. Healthcare Economics Costs of postoperative cerebrospinal fluid leakage: 1-year, retrospective analysis of 412 consecutive nontrauma cases, Surgical Neurology 64 (2005) 490-494.
Johanning JM et al. Femoral artery infections associated with percutaneous arterial closure devices, J Vasc Surg 2001;34:983-985.
Katloff et al. A Comparison of Median Sternotomy and Thoracoscopic Approaches, Chest 110:1399-1406,1996.
Ninan L et al. Adhesive strength of marine mussel extracts of procine skin. Biomaterials 2003;24:4091-4099.
Olivieri MP et al. Surface properties of mussel adhesive protein component films. Biomaterials 1992,13:1000-1008.
Shahidi M et al. Retinal topography and thickness mapping in atrophic age related macular degeneration. Br J Ophthalmol 2002;86:623-626.
Smith TP et al. Infectious complications resulting from use of hemostatic puncture closure devices, Am J Surg 2001;182:658-662.
Swanson et al. J Am. Coll Surg: 185:25-32, 1997.
Toursarkissian B et al. Changing Pattern of Access Site Complications with the Use of Percutaneous Closure Devices, Vasc Endovasc Surg 2001;35:203-206.
Velazquez AJ at el., New dendritic adhesives for sutureless ophthalmic surgical procedures: in viro studies of corneal laceration repair. Arch Ophthalmol 2004;122:867-870.
Agricultural and Biological Chemistry, 1989 (53,10), 2619-2623.
De Joung et al. J. Agric.Food.Chem, 2001(49), 3389-3393.
Gan et al. Food Hydrocolloids 2009 (23), 1398-1405.
Hirose at al. Gelation of Bovine Serum Albumin by Glutathione, J Food Sci, 1990 (55,4) 915-917.
Kang et al. Effect of Disulfide Bond Reduction on Bovine Serum Albumin-Stabilized Emulsion Gel Formed by Microbial Transglutaminase, J Food Sci, 2003 (68,7), 2215-2220.
Lee et al. Agricultural and Biological Chemistry, vol. 55, No. 8 (1991) 2057-2062.
Tobitani et al, Heat-Induced Gelation of Globular Proteins. 1. Model for the Effects of Time and Temperature on the Gelation Time of BSA Gels, Macromolecules, 1997 (30,17), 4845-4854.
Alur HH et al. Transmucosal sustained-delivery of chlorpheniramine maleate in rabbits using a novel, natural mucoadhesive gum as an excipient in buccal tablets, Int. J. Pharm., 1999, 88(1), 1-10.

Babin H et al. Food Hydrocolloids 2001, 15, 271-276.
Bernkop-Schnurch A et al. Pharm. Res., 1999, 16, 6, 876-81.32.
Buchta C et al. Biochemical characterization of autologous fibrin sealants produced by CryoSeal and Vivostat in comparison to the homologous fibrin sealant product Tissucol/Tisseel, Biomaterials 2005, 26, 6233-41.27-30.
Burzio LA et al. Cross-Linking in Adhesive Quinoproteins: Studies with Model Decapeptides, Biochemistry 2000, 39, 11147-53.
Deacon MP et al. Structure and Mucoadhesion of Mussel Glue Protein in Dilute Solution, Biochemistry 1998, 37, 14108-12.
Ehrbar M et al. Enzymatic formation of modular cell-instructive fibrin analogs for tissue engineering, Biomaterials 2007, 28, 3856-66.
Fisher MT et al, PNAS 103, 2006: p. 13265-6.
Garcia Y et al. Assessment of cell viability in a three-dimensional enzymatically cross-linked collagen scaffold. J Mater Sci Mater Med. Oct. 2007;18(10):1991-2001.
Ghebremeskel et al 2006, International Journal of Pharmaceutics 328: 119-129.
Glickman M et al. Arch Surg 2002, 137, 326-31.
Gutowska A et al. Anat Rec 2001, 263, 342-349.
Haines-Butterick L et al. Controlling hydrogelation kinetics by peptide design for three-dimensional encapsulation and injectable delivery of cells, Proc Natl Acad Sci U S A 2007, 104, 7791-6.
Hussain I et al, Animal Feed science and Technology, 1996;62 (2), p. 121-129.
Ikura K et al. Biosci Biotechnol Biochem. 66(6), 2002, p. 1412-1414.
Iwata H et al. A novel surgical glue composed of gelatin and N-hydroxysuccinimide activated poly(L-glutamic acid): Part 1. Synthesis of activated poly(L-glutamic acid) and its gelation with gelatin; Biomaterials 1998, 19, 1869-76.
Jackson M. Fibrin sealants in surgical practice: An overview, Am J Surg 2001, 182, 1S-7S.
Juggi JS et al., In-Vivo Studies with a cation Exchange Resin Mixture in the Removal of Excessive Ammonium from the Extracorporeal Circulation System. ANZ J Surg 1968;38 (2) p. 194-201.
Langoth N et al. Development of buccal drug delivery systems based on a thiolated polymer, Int. J. Pharm., 2003, 252, 141-48.
Lehr C et al. Pharma Res., 1992, 9(4), 547-53.
Lim DW et al. In Situ Cross-Linking of Elastin-like Polypeptide Block Copolymers for Tissue Repair; Biomacromolecules 2008, 9, 222-30.
Ma et al. Enhanced biological stability of collagen porous scaffolds by using amino acids as novel cross-linking bridges; Biomaterials. 2004, 25(15): p. 2997-3004.
Mahoney MJ et al. Contrasting effects of collagen and bFGF-2 on neural cell function in degradable synthetic PEG hydrogels; J Biomed Mater Res A 2007, 81, 269-78.
McDowell et al. Rotational Echo Double Resonance Detection of Cross-links Formed in Mussel Byssus under High-Flow Stress; Biol Chem 1999, 274,20293-5.
Motoki M et al. Transglutaminase and its use for food processing; Trends in Food Science & Technology 1998, 9, 204-210.
Nakamura E et al. Role of glutamine and arginase in protection against ammonia-induced cell death in gastric epithelial cells, Am J of Phys. GI and Liver Phys, 2002; 46(6), p. G1264-G1275.
Office Action from related JP 2011-267107 dated Oct. 7, 2014 (translation).
Office Action from related CN 081306558-E dated Oct. 20, 2014 (translation).
Office Action from related CN 091101424-PVE dated Sep. 1, 2014 (translation).
Office Action from related EP 11192607.7 dated Aug. 5, 2014.
OA for EP patent application 07867783.8 dated: Aug. 26, 2011.
PCT Search Report for corresponding PCT application PCT/US07/025726, 2008.
Liu, Yi, et al. "Biomimetic sealant based on gelatin and microbial transglutaminase: an initial in vivo investigation." Journal of Biomedical Materials Research Part B: Applied Biomaterials 91.1 (2009): 5-16.

(56) References Cited

OTHER PUBLICATIONS

Office Action of related JP2012-545517 dated Feb. 17, 2015 (Translated).
Simpson (Proteins and Proteomic: A Laboratory Manual, 2003).
Gelation of B-Lactoglobulin: Effects of Sodium Chloride and Calcium Chloride on the Rheological and Structural Properties of Gels, D.M. Mulvihill, J.E. Kinsella; Food Science, vol. 53, Issue 1, Jan. 1988, pp. 231-236.
PCT Search Report for corresponding PCT application PCT/US07/025726, published Jan. 28, 2010.
Yiming Biological Products Co., Ltd—Products—Transglutaminase—website as of Dec. 14, 2014.
Spotnitz, William D. "Commercial fibrin sealants in surgical care." The American journal of surgery 182.2 (2001): S8-S14.
Babin H; Dickinson E, Food Hydrocolloids, pp. 204-210.
Jegannathan, Kenthorai Raman, Eng-Seng Chan, and Pogaku Ravindra. "Physical and stability characteristics of Burkholderia cepacia lipase encapsulated in κ-carrageenan." Journal of Molecular Catalysis B: Enzymatic 58.1 (2009): 78-83.
Burgess D.J., International Journal of Pharmaceutics, vol. 27, pp. 61-70.
Canadian Office Action dated Feb. 23, 2017 for CA Application No. 2,782,863; pp. 1-5.
Xiong, Youling L., and John E. Kinsella. "Mechanism of urea-induced whey protein gelation." Journal of agricultural and food chemistry 38.10 (1990): 1887-1891.
CN Office Action dated May 22, 2017 for CN Application No. 2015104308800 (6 pages).
EP Office Action dated May 29, 2017 for EP Application No. 11727766.5-1664 (15 pages).
Getz (A Comparison between the Sulfhydryl Reductants Tris(2-carboxyethyl)phosphine and Dithiothreitol for Use in Protein Biochemistry, 1999).
Office Action dated Jun. 29, 2017 for U.S. Appl. No. 14/181,841; (pp. 1-14).
Chen T; Payne GF et al., J Biomed Mater Res B Appl Biomater, (2006), vol. 77, pp. 416-422.
A.E. Pusateri., J. Biomed. Mater. Res. B Appl. Biomater., (Dec. 15, 2003), vol. 70, No. 1, pp. 114-121.
W. D. Spotnitz, Thromb. Haemost, (1995), vol. 74, pp. 482-485.
De Vries et al., Abstract Book of the Second Annual Meeting of the WHS, Richmond, USA, (1992) p. 51.
Fa Weaver et al., Ann. Vasc. Surg., (2002), vol. 16, No. 3, pp. 286-293.
Olsen D et al., 'Recombinant collagen and gelatin for drug delivery', Adv Drug Deliv Rev, (Nov. 28, 2003), vol. 55, No. 12, doi:doi:10.1016/j.addr.2003.08.008, pp. 1547-1567, XP002368792.
A Novel Microbial Transglutaminase Derived From Streptoverticillium Baldaccii, NEGUS SS., PhD Thesis., Griffith University.
Broderick EP et al., 'Enzymatic Stabilization of Gelatin-Based Scaffolds', J Biomed Mater Res, (2005), vol. 72B, pp. 37-42.
Groenen, P.; Smulders, R; Peters, R. F. R; Grootjans, J. J.; Vandenijssel, P.; Bloemendal, H.; Dejong, W. W., The amine-donor substrate secificity of tissue-type transglutaminase Influence of amino acid residues flanking the amine-donor lysine residue, Eur. J. Biochem., (1994), vol. 220, pp. 795-799.
Mahoney MJ; Anseth KS., J Biomed Mater Res A, (2007), vol. 81, pp. 269-278.
Pursifull, Nathan F., and Allen F. Morey. "Tissue glues and nonsuturing techniques." Current opinion in urology 17.6 (2007): 396-401.
Tissue Adhesives in Clinical Medicine.
Tissue Glue in Cosmetic Surgery, Quality Medical Publishing, Inc.
Otani Y; Tabata Y; Ikada Y, Ann Thorac Surg, (1999), vol. 67, pp. 922-926.
Otani, Y.; Tabata, Y.; Ikada, Y., Biomaterials, (1998), vol. 19, pp. 2167-2173.
Ellis-Behnke RG; Liang YX; Tay DK; Kau PW; Schneider GE; Zhang S; Wu W; So KF, Nanomedicine, (2006), vol. 2, pp. 207-215.
Buchta C; Hedrich HC; Macher M; Hocker P; Redl H., Biomaterials, (2005), vol. 26, pp. 6233-6241, 27, 30.

Wittman M et al., "Biophysical and Transfection Studies of an Amine-Modified Poly(vinyl alcohol) for Gene Delivery", Bioconjugate Chem., (2005), vol. 16, No. 6, pp. 1390-1398.
Shah KU; Rocca JG., Drug Deliv. Tech., (2004), vol. 4, No. 5, p. 1.
Lehr C; Bouwstra JA; Kok W; Noach AB; De Boer AG; Junginger HE, Pharma Res., (1992), vol. 9, No. 4, pp. 547-553.
Alur HH; Pather SI; Mitra AK; Johnston TP, Int. J. Pharm., (1999), vol. 88, No. 1, pp. 1-10.
Deglin JH et al., "Lactulose", Davis's Drug Guide for Nurses, (2003), pp. 589-590.
Fiedler, H. P., Lexikon der Hilfsstoffe fur Pharmazie, Kosmetic and Angrenzende Gebiete, pp. 1300-1304.
SAS Institute Inc. 2004. SAS/STAT® 9.1 User's Guide. Cary, NC: SAS Institute Inc.
Hu, Bi-Huang, and Phillip B. Messersmith. "Rational design of transglutaminase substrate peptides for rapid enzymatic formation of hydrogels." Journal of the American chemical society 125.47 (2003): 14298-14299.
Bauer N; Koehler P; Wieser H; Schieberle P., 'Studies on Effects of Microbial Transglutaminase on Gluten Proteins of Wheat II Rheological Properties', Cereal Chem., vol. 80, No. 6, pp. 787-790.
Sakai S; Kawakami K., "Synthesis and characterization of both ionically and enzymatically crosslinkable alginate", Acta Biomater, (2007), vol. 3, pp. 495-501.
Allen TM et al., JPET, (1985), vol. 234, pp. 250-254.
Villalonga, Reynaldo, Maria L. Villalonga, and Leissy Gómez. "Preparation and functional properties of trypsin modified by carboxymethylcellulose." Journal of Molecular Catalysis B: Enzymatic 10.5 (2000): 483-490.
Chen, Sz-Hau, et al. "Reversible immobilization of lysozyme via coupling to reversibly soluble polymer." Enzyme and Microbial Technology 33.5 (2003): 643-649.
Luchter-Wasylewska E et al., Biotechnology and Applied Biochemistry, (1991), vol. 13, pp. 36-47.
Huang, Xiaolin L., George L. Catignani, and Harold E Swaisgood. "Immobilization of biotinylated transglutaminase by bioselective adsorption to immobilized avidin and characterization of the immobilized activity." Journal of agricultural and food chemistry 43.4 (1995): 895-901.
Marc Suttei; Juergen Siepmann; Wim E. Hennink; Wim Jiskoot, 'Recombinant gelatin hydrogels for the sustained release of proteins', Journal of Controlled Release, (Jun. 22, 2007), vol. 119, No. 3, doi: doi:10.1016/j.jconrel.2007.03.003, pp. 301-312, XP022087330.
Nio N et al: 'Gelation Mechanism of Protein Solution by Transglutaminase' and Biological Chemistry, Japan Soc. for Bioscience, Biotechnology and Agrochem, Tokyo, JP pp. 851-855, 1985.
R. Lerner et ak. (1990). J. Durge. Res 48:165-181.
OA for EP patent application 07867783.8 dated: Jan. 28, 2010.
PCT Search Report for corresponding PCT application PCT/US071025726.
Translation of office action from corresponding Chinese application No. 201110365186.7, dated Dec. 23, 2013.
Office Action for CN 102124058 A dated May 9, 2013.
Office Action for CN 101854960 A dated Apr. 3, 2013.
Office Action for JP2011-267107 dated Jul. 23, 2013.
Office action from corresponding Chinese application No. CN 201080057151.0, dated Nov. 27, 2013 (original Chinese language document).
OA for EP11192607.7 dated Jan. 2, 2013.
Search report issued for corresponding EP Application No. 11192607.7 dated May 10, 2012.
Office Action of related JP2013265507 dated Jan. 20, 2015 (Translated).
Simpson, Richard J. Proteins and Proteomics: A Laboratory Manual. Cold Spring Habor Laboratory Press, 2003. p. 350.
PCT Search Report for corresponding PCT application PCT/US07/025726.
Matsuura et al. "Activity and Stability of Microbial Transglutaminase Modified with a Water-Soluble Polymer" Kobunshi Ronbunshu 58(2) 73-77 (2001).
Ghebremeskel et al 2007, International Journal of Pharmaceutics 328: 119-129.

(56) References Cited

OTHER PUBLICATIONS

Translation of summary of office action from corresponding Chinese application No. CN 201080057151.0.

* cited by examiner

MODIFICATION OF ENZYMATIC CROSSLINKERS FOR CONTROLLING PROPERTIES OF CROSSLINKED MATRICES

BACKGROUND

Utility of Enzyme Crosslinked Matrices

Enzyme crosslinked matrices are formed in a variety of applications in the food, cosmetic, and medical industries. In medical applications in particular, enzyme crosslinked hydrogels are widely used in a variety of medical applications including tissue sealants and adhesives, haemostatic preparations, matrices for tissue engineering or platforms for drug delivery. While some hydrogels such as gelatin and poloxamer may be formed as a result of physical interactions between the polymer chains under specific conditions, e.g change in temperature, most polymer solutions must be crosslinked in order to form hydrogels. In addition to the actual formation of the solid gel, implantable hydrogels must be resistant to the conditions that are prevalent in the tissue where they are applied, such as mechanical stress, temperature increase, and enzymatic and chemical degradation. For this reason, in many cases it is necessary to crosslink the hydrogel matrices. The crosslinking may be done outside the body by pre-casting or molding of hydrogels. This application is used mainly for tissue engineering or drug delivery applications. Alternatively, crosslinking may be done inside the body (in situ gelation or cross linking) where a liquid solution is injected or applied to the desired site and is cross linked to form a gel.

Gel formation can be initiated by a variety of crosslinking approaches. Chemical approaches to gel formation include the initiation of polymerization either by contact, as in cyanoacrylates, or external stimuli such as photo-initiation. Also, gel formation can be achieved by chemically cross-linking pre-formed polymers using either low molecular weight crosslinkers such as glutaraldehyde or carbodiimide (Otani Y, Tabata Y, Ikada Y. Ann Thorac Surg 1999, 67, 922-6. Sung H W, Huang D M, Chang W H, Huang R N, Hsu J C. J Biomed Mater Res 1999, 46, 520-30. Otani, Y.; Tabata, Y.; Ikada, Y. Biomaterials 1998, 19, 2167-73. Lim, D. W.; Nettles, D. L.; Setton, L. A.; Chilkoti, A. Biomacromolecules 2008, 9, 222-30.), or activated substituents on the polymer (Iwata, H.; Matsuda, S.; Mitsuhashi, K.; Itoh, E.; Ikada, Y. Biomaterials 1998, 19, 1869-76).

However, chemical crosslinking can be problematic in food, cosmetic, or medical applications because the cross-linkers are often toxic, carcinogenic, or irritants. Furthermore, they are small molecules that can readily diffuse out of the crosslinked matrix and might cause local or systemic damage.

An alternative to chemical crosslinking is the enzymatic crosslinking approach. These approaches to initiate gel formation have been investigated based on a variety of different crosslinking enzymes. Examples include enzymatic crosslinking of adhesives, such as mussel glue (Strausberg R L, Link R P. Trends Biotechnol 1990, 8, 53-7), or the enzymatic crosslinking of blood coagulation, as in fibrin sealants (Jackson M R. Am J Surg 2001, 182, 1S-7S. Spotnitz W D. Am J Surg 2001, 182, 8S-14S Buchta C, Hedrich H C, Macher M, Hocker P, Redl H. Biomaterials 2005, 26, 6233-41.27-30).

Cross-linking of a mussel glue was initiated by the enzymatic conversion of phenolic (i.e., dopa) residues of the adhesive protein into reactive quinone residues that can undergo subsequent inter-protein crosslinking reactions (Burzio L A, Waite J H. Biochemistry 2000, 39, 11147-53. McDowell L M, Burzio L A, Waite J H, Schaefer J J. Biol Chem 1999, 274, 20293-5). The enzymes which have been employed in this class of sealants are tyrosinase on one hand and laccase and peroxidase on the other hand which acts by forming quinones and free radicals, respectively from tyrosine and other phenolic compounds. These in turn can crosslink to free amines on proteins or to similarly modified phenolic groups on proteins and polysaccharides.

A second cross-linking operation that has served as a technological model is the transglutaminase-catalyzed reactions that occur during blood coagulation (Ehrbar M, Rizzi S C, Hlushchuk R, Djonov V, Zisch A H, Hubbell J A, Weber F E, Lutolf M P. Biomaterials 2007, 28, 3856-66). Biomimetic approaches for in situ gel formation have investigated the use of Factor XIIIa or other tissue transglutaminases (Sperinde J, Griffith L. Macromolecules 2000, 33, 5476-5480. Sanborn T J, Messersmith P B, Barron A E. Biomaterials 2002, 23, 2703-10).

An additional in situ crosslinked gel formation of particular interest is the crosslinking of gelatin by a calcium independent microbial transglutaminase (mTG). mTG catalyzes an analogous crosslinking reaction as Factor XIIIa but the microbial enzyme requires neither thrombin nor calcium for activity. Initial studies with mTG were targeted to applications in the food industry (Babin H, Dickinson E. Food Hydrocolloids 2001, 15, 271-276. Motoki M, Seguro K. Trends in Food Science & Technology 1998, 9, 204-210.), while later studies considered potential medical applications. Previous in vitro studies have shown that mTG can crosslink gelatin to form a gel within minutes, the gelatin-mTG adhesive can bond with moist or wet tissue, and the adhesive strength is comparable to, or better than, fibrin-based sealants (Chen T H, Payne G F, et al. Biomaterials 2003, 24, 2831-2841. McDermott M K, Payne G F, et al. Biomacromolecules 2004, 5, 1270-1279. Chen T, Payne G F, et al. J Biomed Mater Res B Appl Biomater 2006, 77, 416-22.). The use of gelatin and mTG as a medical adhesive is described in PCT WO/2008/076407.

One of the disadvantages of using enzymes as the cross-linkers in crosslinked matrix formation is that they may continue the cross linking reaction after the desired gel state has been formed. This is often not desired because excessive cross linking may result in a stiffer, more brittle, and less flexible gel. In addition, the mechanical properties of the crosslinked matrix will continue to change during the lifetime of the gel, making consistent properties difficult to achieve. The continued enzymatic cross linking beyond the desired crosslinking density results from the ability of the enzyme to continue to catalyze the crosslinking reaction even once a crosslinked matrix or hydrogel has been formed. This depends on the ability of the enzyme to continue to diffuse throughout the matrix even as solution viscosity increases greatly. This view is consistent with Hu et al (Hu B H, Messersmith P B. J. Am. Chem. Soc., 2003, 125 (47), pp 14298-14299) who suggested, based on work done with peptide-grafted synthetic polymer solutions, that during incipient network formation resulting from partial cross-linking of a polymer solution, the solution viscosity rapidly increases while the mobility of the transglutaminase rapidly decreases.

The problem of excessive enzymatic crosslinking leading to a reduction in mechanical properties has been previously documented on several occasions:

Bauer et al. demonstrated that high levels of microbial transglutaminase (mTG) caused excessive cross-linking of wheat gluten proteins leading to a loss of elasticity and mechanical damage of the gluten networks. (Bauer N, Koehler P, Wieser H, and Schieberle P. Studies on Effects of Microbial Transglutaminase on Gluten Proteins of Wheat II Rheological Properties. Cereal Chem. 80(6):787-790).

Sakai et al. found that a larger quantity of covalent cross-linking between phenols was effective for enhancement of the mechanical stability, however, further cross-linking between the phenols resulted in the formation of a brittle gel. (Sakai S, Kawakami K. Synthesis and characterization of both ionically and enzymatically crosslinkable alginate, Acta Biomater 3 (2007), pp. 495-501)

In the case of cofactor-dependent crosslinking enzymes, such as calcium-dependent transglutaminase, removing the cofactor, by binding or otherwise, after a certain reaction time can limit the degree of crosslinking. However, cofactor removal is frequently not technically feasible in hydrogel formation where the hydrogel may trap the cofactor. When using cofactor-independent enzymes, such as transglutaminases available from microbial origin, limited degrees of crosslinking can be obtained by heat treatment of the reaction system. However, such a treatment induces negative side effects on protein functionality and is therefore undesirable to apply. In addition, not all reaction systems are suitable to undergo heat treatment.

Other than resulting in excessive crosslinking within the crosslinked matrix, continued diffusion of the crosslinked enzyme in the matrix after the desired crosslinked state has been achieved also can result in a high rate of enzyme diffusion out of the gel, also known as enzyme elution. This can also be problematic as high levels of crosslinking enzyme released into the body can interact with body tissues and cause local or systemic damage.

SUMMARY OF INVENTION

There is a need for, and it would be useful to have, an improved enzyme crosslinked composition which could be used for a wide variety of applications.

Therefore, there is a need for, and it would be useful to have a mechanism to stop enzymatic cross linking of crosslinked matrices following the initial formation of the solid matrix at a point where the desired mechanical properties have obtained; and/or to reduce the extent and rate of elution of the enzyme from the solid crosslinked matrix.

The present invention, in at least some embodiments, overcomes the above described drawbacks of the background art, and provides a solution to the above technical problems (among its many advantages and without wishing to provide a closed list), by providing a matrix or hydrogel that is formed by enzymatic crosslinking of polymers wherein the crosslinking enzyme molecules have been modified for the purpose of improving the crosslinking density, mechanical properties, or other properties of the matrix, and/or to provide improved control over the rate and/or extent of crosslinking.

An optional method of altering the enzyme molecules is by modifying the perceived volume of the enzyme molecules in the crosslinked matrix being formed. The modified perceived volume is preferably determined according to the extent of crosslinking of the polymers to form the matrix, such that decreased extent of crosslinking, as compared with extent of crosslinking with unmodified enzyme molecules, indicates increased perceived volume.

One method of increasing the perceived volume of the enzyme molecules is by increasing the size and/or the hydrodynamic volume of the molecules by covalent or non-covalent attachment of at least one molecule or moiety to the enzyme molecules. The inventors have demonstrated that the degree of enzymatic crosslinking in hydrogels or crosslinked matrices can be regulated by covalent attachment of molecules to the enzyme such that the modification of the enzyme molecules result in a lower ultimate level of crosslinking. In this manner, the phenomenon of excessive crosslinking can be prevented.

Another method of increasing the perceived volume is through modification of the electrostatic charge of the enzyme molecules such that their net charge is of opposite sign to the net charge on the polymer or co-polymer chains. This can be achieved by changing the isoelectric point (pI) of the enzyme.

In a non-limiting hypothesis, increasing the perceived volume of the enzyme molecules reduces the mobility or diffusion of the molecules in the crosslinked matrix or hydrogel. This prevents it from continuing its crosslinking activity beyond the point where the crosslinking is beneficial to the desired material properties of the hydrogel.

"Perceived volume" or "effective volume" as defined herein refers to the effective hydrodynamic volume of the crosslinking enzyme inside the crosslinked matrix. The perceived volume may be increased by covalent or non-covalent binding of the enzyme to another molecule, carrier, polymer, protein, polysaccharide and others, prior to the crosslinking reaction or during the crosslinking reaction.

"Diffusion" or "Mobility" as defined herein refers to the random molecular motion of the crosslinking enzyme or other proteins, in solution, hydrogen, or matrix that result from Brownian motion.

"Diffusion coefficient" as defined herein refers to a term that quantifies the extent of diffusion for a single type of molecule under specific conditions. A non-limiting example of a proxy for measuring enzyme diffusion is by measuring the elution of enzyme from a hydrogel.

"Reduced Mobility" as defined herein refers to a slower molecular motion or smaller diffusion coefficient of a protein or enzyme in a solution or inside a hydrogel.

"Size" as defined herein refers to the molecular weight or hydrodynamic volume or perceived volume of a molecule.

"Molecular weight", abbreviated as MW, as used herein refers to the absolute weight in Daltons or kilodaltons of proteins or polymers. For example, the MW of a PEGylated protein (ie—protein to which one or more PEG (polyethylene glycol) molecules have been coupled) is the MW sum of all of its constituents.

"Hydrodynamic Volume" as defined herein refers to the apparent molecular weight of a protein or enzyme that may usually be measured using size exclusion chromatography. The hydrodynamic volume of a constituent refers to the diameter or volume the constituent assumes when it is in motion in a liquid form.

"Matrix" as defined herein refers to refers to a composition of crosslinked materials. Generally, when the matrix-forming materials are crosslinked, the composition that includes these materials transitions from a liquid state to a gel state, thereby forming a "gel," "hydrogel" or a "gelled composition." The gel can have certain viscoelastic and rheological properties that provide it with certain degrees of durability and swellability. These materials are often polymers. The matrix may contain materials which are not crosslinked, sometimes referred to as co-polymers.

"Polymer" as used herein refers to a natural, synthetic or semi-synthetic molecule, containing a repeatable unit.

"Co-polymer" as used herein refers to a constituent of the matrix which may or may not participate in the crosslinking reaction and is usually not the main constituent of the matrix. A non-limiting example comprises polysaccharides such as dextran and/or a cellulosic polymer such as carboxymethyl cellulose. The co-polymer is preferably not covalently bound to the enzyme or to the matrix material, such as the protein base of the matrix.

"Carrier" as used herein refers to a polymer, a protein, polysaccharide or any other constituent which binds the crosslinking enzyme covalently or non-covalently, either before or during the crosslinking reaction.

"Crosslinking Enzyme" as defined herein refers to an enzyme or combination of enzymes that can either directly (e.g. by transglutamination) or indirectly (e.g. through quinone or free radical formation) crosslink substrate groups on polymer strands into a coherent matrix, such as a hydrogel.

According to at least some embodiments of the present invention, there is provided a cross-linked matrix, comprising a substrate polymer crosslinked by a modified enzyme molecule, said modified enzyme molecule having a modification that alters a perceived volume of the enzyme molecules in the crosslinked matrix as the matrix is being formed through cross-linking of said polymer.

Optionally said modified enzyme molecule has a modification that increases an actual size of said modified enzyme molecule. Optionally said modified enzyme molecule has a modification that increases a hydrodynamic volume of said modified enzyme molecule. Optionally said modified enzyme molecule has a modification that modifies an electrostatic charge of said modified enzyme molecule to be of opposite sign to a net charge of said substrate polymer by changing the isoelectric point (pI) of said modified enzyme in comparison to unmodified enzyme. Optionally said modification is of the ε-amino group of lysines of the enzyme through a process selected from the group consisting of succinylation (with succinic anhydride), acetylation (with acetic anhydride), carbamylation (with cyanate), reductive alkylation (aldehydes) and treatment with maleic anhydride. Optionally said modification is of one or more side chains containing carboxylic acids of the enzyme to decrease the number of negative charges.

Optionally said modification comprises covalent or non-covalent attachment of at least one molecule or moiety to said modified enzyme molecule. Optionally said modification comprises covalent attachment of a modifying molecule to said modified enzyme molecule. Optionally said modified enzyme molecule has a reduced diffusion rate and a reduced cross-linking rate in comparison to non-modified enzyme, but has at least similar measured enzyme activity in comparison to non-modified enzyme.

Optionally reduced cross-linking rate is at least 10% of the non-modified enzyme cross-linking rate.

Optionally said modifying molecule comprises a carrier or polymer. Optionally said polymer comprises a synthetic polymer, a cellulosic polymer, a protein or a polysaccharide. Optionally said cellulosic polymer comprises one or more of carboxymethyl cellulose, hydroxypropyl methylcellulose, hydroxyethyl cellulose, or methyl cellulose. Optionally said polysaccharide comprises one or more of dextran, chondroitin sulfate, dermatan sulfate, keratan sulfate, heparin, heparan sulfate, hyaluronic acid or a starch derivative.

Optionally said modifying molecule comprises PEG (polyethylene glycol). Optionally said PEG comprises a PEG derivative. Optionally said PEG derivative comprises activated PEG. Optionally said activated PEG comprises one or more of methoxy PEG (mPEG), its derivatives, mPEG-NHS, succinimidyl (NHS) esters of mPEG (mPEG-succinate-NHS), mPEG-glutarate, -NHS, mPEG-valerate-NHS, mPEG-carbonate-NHS, mPEG-carboxymethyl-NHS, mPEG-propionate-NHS, mPEG-carboxypentyl-NHS), mPEG-nitrophenylcarbonate, mPEG-propylaldehyde, mPEG-Tosylate, mPEG-carbonylimidazole, mPEG-isocyanate, mPEG-epoxide or a combination thereof. Optionally said activated PEG reacts with amine groups or thiol groups on said enzyme. Optionally the molar ratio of said activated PEG to lysine residues of said activated enzyme is in a range of from 0.5 to 25. Optionally said activated PEG is monofunctional, heterobifunctional, homobifunctional, or multifunctional. Optionally said activated PEG is branched PEGs or multi-arm PEGs. Optionally said activated PEG has a size ranging from 1000 dalton to 40,000 dalton.

Optionally the matrix further comprises a co-polymer that is not covalently bound to said enzyme or to said substrate polymer. Optionally said co-polymer comprises a polysaccharide or a cellulosic polymer. Optionally said polysaccharide comprises dextran, chondroitin sulfate, dermatan sulfate, keratan sulfate, heparin, heparan sulfate, hyaluronic acid or a starch derivative. Optionally said cellulosic polymer comprises carboxymethyl cellulose, hydroxypropyl methylcellulose, hydroxyethyl cellulose, methyl cellulose.

Optionally said modified enzyme molecule is modified by cross-linking said modified enzyme molecule to a plurality of other enzyme molecules to form an aggregate of a plurality of cross-linked enzyme molecules.

Optionally a modification or an extent of modification of said modified enzyme molecule affects at least one property of the matrix. Optionally said at least one property is selected from the group consisting of tensile strength, stiffness, extent of crosslinking of said substrate polymer, viscosity, elasticity, flexibility, strain to break, stress to break, Poisson's ratio, swelling capacity and Young's modulus, or a combination thereof.

Optionally an extent of modification of said modified enzyme determines mobility of said modified enzyme in, or diffusion from, the matrix. Optionally said modification of said modified enzyme reduces diffusion coefficient of said modified enzyme in a solution of said modified enzyme and said protein or in a matrix of said modified enzyme and said protein, in comparison to a solution or matrix of non-modified enzyme and said protein. Optionally an extent of modification of said modified enzyme determines one or more matrix mechanical properties. Optionally said modified enzyme molecule shows a greater differential of cross-linking rate in crosslinked polymer than in solution as compared to non-modified enzyme molecule.

According to at least some embodiments of the present invention, there is provided a method for controlling formation of a matrix, comprising modifying an enzyme molecule with a modification that alters a perceived volume of the enzyme molecules in the crosslinked matrix as the matrix is being formed; mixing said modified enzyme molecule with at least one substrate polymer that is a substrate of said modified enzyme molecule; and forming the matrix through crosslinking of said at least one substrate polymer by said modified enzyme molecule, wherein said forming the matrix is at least partially controlled by said modification of said enzyme molecule. Optionally said modification reduces a crosslinking rate of said modified enzyme molecule as an extent of crosslinking of said at least one substrate polymer increases. Optionally said modified enzyme molecule and said at least one substrate polymer are mixed in solution, such that said modification controls extent of crosslinking of said at least one substrate polymer as a viscosity of said solution increases. Optionally said modifying comprises PEGylation of the enzyme at a pH in a range from 7 to 9. Optionally pH of the PEGylation reaction is 7.5-8.5.

According to at least some embodiments for the method and/or matrix, said at least one substrate polymer comprises a substrate polymer selected from the group consisting of a naturally cross-linkable polymer, a partially denatured polymer that is cross-linkable by said modified enzyme and a modified polymer comprising a functional group or a peptide that is cross-linkable by said modified enzyme. Optionally said at least one substrate polymer comprises gelatin, collagen, casein or albumin, or a modified polymer, and wherein said modified enzyme molecule comprises a modified transglutaminase and/or a modified oxidative enzyme. Optionally said at least one substrate polymer comprises gelatin selected from the group consisting of gelatin obtained by partial hydrolysis of animal tissue or collagen obtained from animal tissue, wherein said animal tissue is selected from the group consisting of animal skin, connective tissue, antlers, horns, bones, fish scales, and a recombinant gelatin produced using bacterial, yeast, animal, insect, or plant systems or any type of cell culture, or any combination thereof. Optionally said gelatin is of mammalian or fish origin. Optionally said gelatin is of type A (Acid Treated) or of type B (Alkaline Treated). Optionally said gelatin is of 250-300 bloom. Optionally said gelatin has an average molecular weight of 75-150 kda.

Optionally said modified transglutaminase comprises modified microbial transglutaminase. Optionally said modified polymer is modified to permit crosslinking by said modified microbial transglutaminase. Optionally said modified oxidative enzyme comprises one or more of tyrosinase, laccase, or peroxidase. Optionally said matrix further comprises a carbohydrate comprising a phenolic acid for being cross-linked by said modified oxidative enzyme as said at least one substrate polymer. Optionally said carbohydrate comprises one or more of arabinoxylan or pectin. Optionally said enzyme molecule is modified through PEGylation and wherein said PEGylation provides immunogenic masking by masking said enzyme molecule from an immune system of a host animal receiving the matrix. Optionally said host animal is human.

According to at least some embodiments, there is provided a method for sealing a tissue against leakage of a body fluid, comprising applying a matrix as described herein to the tissue. Optionally said body fluid comprises blood, such that said matrix is a hemostatic agent.

According to at least some embodiments, there is provided a hemostatic agent or surgical sealant, comprising a matrix as described herein.

According to at least some embodiments, there is provided a composition for sealing a wound, comprising a matrix as described herein. According to at least some embodiments, there is provided a use of the composition for sealing suture or staple lines in a tissue.

According to at least some embodiments, there is provided a composition for a vehicle for localized drug delivery, comprising a matrix as described herein.

According to at least some embodiments, there is provided a composition for tissue engineering, comprising a matrix as described herein, adapted as an injectable scaffold.

According to at least some embodiments, there is provided a method of modifying a composition, comprising: providing a modified enzyme having a cross-linkable functional group and a protein having at least one moiety cross-linkable by said modified enzyme; mixing said modified enzyme and said protein, wherein said modified enzyme cross-links said protein and is also cross-linked to said protein through said cross-linkable functional group.

Non-limiting examples of direct crosslinking enzymes, which directly crosslink substrate groups on polymer strands, include transglutaminases and oxidative enzymes. Examples of transglutaminases include microbial transglutaminase (mTG), tissue transglutaminase (tTG), and Factor XIII. These enzymes can be from either natural or recombinant sources. Glutamine and lysine amino acids in the polymer strands are substrates for transglutaminase crosslinking.

Non-limiting examples of oxidative enzymes are tyrosinase, laccase, and peroxidase. These enzymes crosslink polymers by quinone formation (tyrosinase) or free radical formation (laccase, peroxidase). The quinones and the free radicals then interact with each other or with other amino acids or phenolic acids to crosslink the polymers. The crosslinkable substrates for these enzymes may be any proteins which contain tyrosine or other aromatic amino acids. The substrates may also be carbohydrates which contain phenolic acids such as freulic acid. Such carbohydrates may be arabinoxylan or pectin, for example.

Synthetic or partially synthetic polymers with one or more suitable functional groups could also serve as cross-linkable substrates for any of the above enzymes.

In another embodiment of the present invention, a combination of enzymes is used.

"Polymer strands" or "Polymer chains" as defined herein refers to the substrate polymer for enzyme crosslinking, which according to at least some embodiments of the present invention, preferably belongs to one of the below categories (as non-limiting examples only and without wishing to provide a closed list):

1) Any polymer with substrate groups that are naturally crosslinkable by the enzyme and that is itself naturally crosslinkable by the enzyme. For example, in the case of transglutaminases, this would include protein or polypeptides such as gelatin, collagen, and casein which are naturally crosslinkable by the enzyme.
2) Polymers which contain substrate groups crosslinkable by the enzyme but which are not naturally crosslinkable by the enzyme as a result of their structure. In such cases, the polymer structure must be modified prior to enzyme crosslinking. For example, in the case of transglutaminases, this would include proteins, such as albumin or lactoglobulin, which are not natural substrates for the enzyme because they have a globular structure which hinders the access of the enzyme. These can be made into substrates by partially denaturing the protein using reducing agents, denaturing agents or heat.
3) Polymers, natural or synthetic, that are not substrates for enzyme crosslinking but that have been modified with peptides or functional groups which are substrates of the enzyme, thus rendering the modified polymer crosslinkable by the enzyme.

Non-limiting examples of such polymers include any suitable type of protein, which may for example optionally comprise gelatin as noted above. Gelatin may optionally comprise any type of gelatin which comprises protein that is known in the art, preferably including but not limited to gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture.

According to preferred embodiments of the present invention, gelatin from animal origins preferably comprises gelatin from mammalian origins and more preferably comprises one or more of pork skins, pork and cattle bones, or split cattle hides, or any other pig or bovine source. More preferably, such gelatin comprises porcine gelatin since it has a lower rate of anaphylaxis. Gelatin from animal origins may optionally be of type A (Acid Treated) or of type B (Alkaline Treated), though it is preferably type A.

Preferably, gelatin from animal origins comprises gelatin obtained during the first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. Preferably, 275-300 bloom gelatin is used.

A non-limiting example of a producer of such gelatins is PB Gelatins (Tessenderlo Group, Belgium).

According to some embodiments of the present invention, gelatin from animal origins optionally comprises gelatin from fish. Optionally any type of fish may be used, preferably a cold water variety of fish such as carp, cod, or pike, or tuna. The pH of this gelatin (measured in a 10% solution) preferably ranges from 4-6.

Cold water fish gelatin forms a solution in water at 10° C. and thus all cold water fish gelatin are considered to be 0 bloom. For the present invention, a high molecular weight cold water fish gelatin is optionally and preferably used, more preferably including an average molecular weight of at least about 95-115 kDa. This is equivalent to the molecular weight of a 250-300 bloom animal gelatin. Cold water fish gelatin undergoes thermoreversible gelation at much lower temperatures than animal gelatin as a result of its lower levels of proline and hydroxyproline. Per 1000 amino acid residues, cold water fish gelatin has 100-130 proline and 50-75 hydroxyproline groups as compared to 135-145 proline and 90-100 hydroxyproline in animal gelatins (Haug L T, Draget K I, Smidsrød O. (2004). Food Hydrocolloids. 18:203-213).

A non-limiting example of a producer of such a gelatin is Norland Products (Cranbury, N.J.).

In some embodiments of the present invention, low endotoxicity gelatin is used to form the gelatin solution component of the gelatin-mTG composition. Such a gelatin is available commercially from suppliers such as Gelita™ (Eberbach, Germany). Low endotoxicity gelatin is defined as gelatin with less than 1000 endotoxicity units (EU) per gram. More preferably, gelatin of endotoxicity less than 500 EU/gram is used.

For very high sensitivity applications, such as with materials that will come into contact with either the spine or the brain, gelatin with endotoxicity of less than 100 EU/gram is preferred, gelatin with less than 50 EU/g is more preferred. Gelatin with endotoxicity less than 10 EU/g is very expensive but could also be used as part of at least some embodiments of the present invention in sensitive applications.

According to some embodiments of the present invention, type I, type II, or any other type of hydrolyzed or non-hydrolyzed collagen replaces gelatin as the protein matter being cross-linked. Various types of collagen have demonstrated the ability to form thermally stable mTG-crosslinked gels.

According to some embodiments of the present invention, a recombinant human gelatin is used. Such a gelatin is available commercially from suppliers such as Fibrogen™ (San Francisco, Calif.). Recombinant gelatin is preferably at least about 90% pure and is more preferably at least about 95% pure. Some recombinant gelatins are non-gelling at 10° C. and thus are considered to be 0 bloom. For some embodiments of the present invention, a high molecular weight recombinant gelatin is preferably used, more preferably including a molecular weight of at least about 95-100 kDa.

As noted above, the cross-linkable protein preferably comprises gelatin but may also, additionally or alternatively, comprise another type of protein. According to some embodiments of the present invention, the protein is also a substrate for transglutaminase, and preferably features appropriate transglutaminase-specific polypeptide and polymer sequences. These proteins may optionally include but are not limited to synthesized polymer sequences that independently have the properties to form a bioadhesive or polymers that have been more preferably modified with transglutaminase-specific substrates that enhance the ability of the material to be cross-linked by transglutaminase. Non-limiting examples of each of these types of materials are described below.

Synthesized polypeptide and polymer sequences with an appropriate transglutaminase target for cross-linking have been developed that have transition points preferably from about 20 to about 40° C. Preferred physical characteristics include but are not limited to the ability to bind tissue and the ability to form fibers Like gelling type gelatins (described above), these polypeptides may optionally be used in compositions that also feature one or more substances that lower their transition point.

Non-limiting examples of such peptides are described in U.S. Pat. Nos. 5,428,014 and 5,939,385, both filed by ZymoGenetics Inc, both of which are hereby incorporated by reference as if fully set forth herein. Both patents describe biocompatible, bioadhesive, transglutaminase cross-linkable polypeptides wherein transglutaminase is known to catalyze an acyl-transfer reaction between the γ-carboxamide group of protein-bound glutaminyl residues and the ε-amino group of Lys residues, resulting in the formation of ε-(γ-glutamyl) lysine isopeptide bonds.

According to some embodiments, the resultant composition is used as a vehicle for localized drug delivery.

According to some embodiments, the resultant composition is an injectable scaffold for tissue engineering.

According to some embodiments, the composition is a hemostatic composition. According to some embodiments, the composition is a body fluid sealing composition.

The compositions of the present invention preferably provide rapid hemostasis, thereby minimizing blood loss following injury or surgery.

"Wound" as used herein refers to any damage to any tissue of a patient that results in the loss of blood from the circulatory system or the loss of any other bodily fluid from its physiological pathway, such as any type of vessel. The tissue can be an internal tissue, such as an organ or blood vessel, or an external tissue, such as the skin. The loss of blood or bodily fluid can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

Surgical wound closure is currently achieved by sutures and staples that facilitate healing by pulling tissues together. However, very often they fail to produce the adequate seal necessary to prevent fluid leakage. Thus, there is a large, unmet medical need for devices and methods to prevent leakage following surgery, including leaks that frequently occur along staple and suture lines. Such devices and methods are needed as an adjunct to sutures or staples to achieve hemostasis or other fluid-stasis in peripheral vascular reconstructions, dura reconstructions, thoracic, cardiovascular, lung, neurological, and gastrointestinal surgeries. Most high-pressure hemostatic devices currently on the market are nominally, if at all adhesive. Thus, the compositions of the present invention, according to at least some embodiments, overcome these drawbacks and may optionally be used for hemostasis.

As used herein, "about" means plus or minus approximately ten percent of the indicated value.

Other features and advantages of the various embodiments of the invention will be apparent from the following detailed description, and from the claims.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF INVENTION

Figure 1:
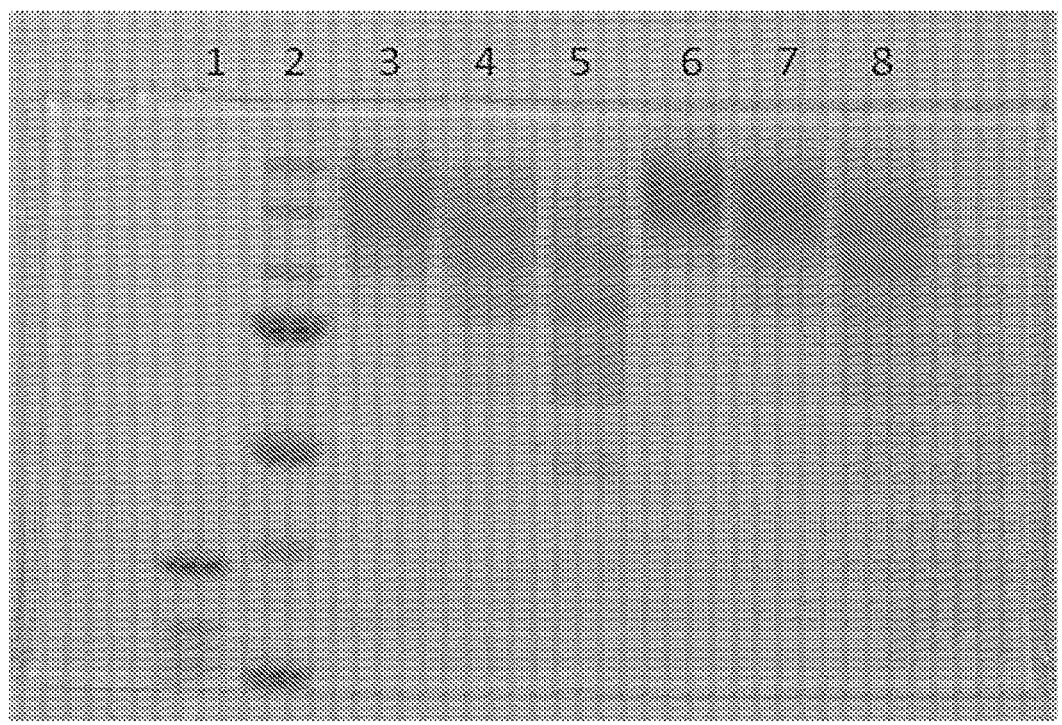
FIG. 1: Effect of reaction pH and activated PEG concentration on PEGylation products size and distribution.

The section headings that follow are provided for ease of description only. It is to be understood that they are not intended to be limiting in any manner. Also, unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Increased Perceived Volume of Enzyme Crosslinker in Hydrogel

It was found that, in addition to the viscosity of the enzyme-containing polymer solution and the crosslinking density of the partially cross linked solution (availability of reactive groups), the catalytic rate of a crosslinking enzyme within a crosslinked matrix can also be controlled through control of the perceived volume of the enzyme molecule.

According to at least some embodiments of the present invention, such control can optionally and preferably lead to reduced catalytic rate of crosslinking as the matrix approaches a desired mechanical state, by increasing the perceived volume of the enzyme molecule prior to initiation of the crosslinking reaction or during the reaction itself. In this manner, the solidifying matrix traps the size-enhanced enzyme at the desired crosslinking density state and further crosslinking is prevented. Perceived enzyme volume is a function of enzyme molecular weight and hydrodynamic volume, among other factors.

The ultimate extent of crosslinking within a crosslinked matrix can be limited by engineering the enzyme molecules, the matrix material, the crosslinking environment, or some combination of these factors to increase the perceived volume of the enzyme molecules within the crosslinked matrix as the matrix is formed. Without wishing to be limited by a single hypothesis, it is possible that increased perceived enzyme volume results in reduced mobility of the enzyme in the crosslinked matrix. Reducing enzyme mobility to control ultimate crosslinking density is most effective when the enzyme molecules maintain mobility at the early crosslinking reaction stages when the solution viscosity is still low, but lose mobility as crosslinking progresses to increase the solution viscosity, and lose mobility more severely after the initial solid matrix or hydrogel has been formed. Naturally, the precise levels of enzyme mobility within the matrix should be regulated to achieve the crosslinking profile and extent desirable for a particular application.

Without wishing to be limited by a single hypothesis, an enzyme with an increased size or increased hydrodynamic volume has a lower diffusion coefficient or mobility in the crosslinked matrix than the non-modified enzyme, resulting in a more limited access to crosslinkable substrates.

Enzyme Molecules with Increased Size and/or Hydrodynamic Volume

A preferred method of reducing the mobility of enzyme molecules in a crosslinked matrix is increasing the effective size of the enzyme molecules. This can be accomplished by increasing the enzyme molecule molecular weight (MW), hydrodynamic volume, or both MW and hydrodynamic volume. This is a preferred method because it should not affect the structural composition of the crosslinked matrix.

To be effective for the herein described embodiments of the present invention, enzyme molecule size is preferably increased in a manner that does not eliminate enzyme activity or its ability to crosslink the desired polymer substrate into a solid matrix or hydrogel. The enzyme also preferably retains sufficient activity to form the matrix within an appropriate amount of time. Furthermore, the size-enhanced enzyme molecule also preferably retains sufficient mobility within the crosslinked matrix to catalyze the desired degree of crosslinking prior to ceasing mobility within the matrix.

A number of methods have been identified for increasing enzyme molecule size in crosslinked matrices or hydrogels:
1. Cross link the enzyme to itself (intermolecular crosslinking) in order to from soluble multi-unit conjugates. An example of this is described in example 18, below.
2. Covalent binding (immobilization) of the enzyme on a carrier:
   I. Immobilization to a soluble protein, for example albumin; (Allen T M et al, 1985, JPET 234: 250-254, alpha-Glucosidase-albumin conjugates: effect of chronic administration in mice)
   II. Immobilization on a soluble polymer. Preferably, the polymer carrier is larger than the enzyme, where one or more enzyme molecules are immobilized on each molecule of the polymer. It is also possible that a single enzyme molecule will bind to more than one polymer molecule via two or more attachment sites. The carrier may be natural, synthetic or semi-synthetic. Many such applications were developed in order to increase the in vivo stability of enzymes or to reduce immunogenicity. One such family of polymers is cellulose ethers, including but not limited to carboxymethyl cellulose, hydroxypropyl methylcellulose, hydroxyethyl cellulose, methyl cellulose and others. Such immobilization has previously been accomplished with enzymes such as trypsin (Villaonga et al, 2000, Journal of Molecular Catalysis B: 10, 483-490 Enzymatic Preparation and functional properties of trypsin modified by carboxymethylcellulose) and lysozyme (Chen S H et al, 2003, Enzyme and Microbial Technology 33, 643-649, Reversible immobilization of lysozyme via coupling to reversibly soluble polymer), though such enzyme immobilization has never previously been used to affect mechanical properties of enzyme-crosslinked hydrogels or matrices.
   III. Binding to a glycosaminoglycan (GAG), including but not limited to chondroitin sulfate, dermatan sulfate, keratan sulfate, heparin, heparan sulfate, and hyaluronic acid. As above, such binding has been accomplished (Luchter-Wasylewska E et al., 1991, Biotechnology and applied biochemistry 13: 36-47, Stabilization of human prostatic acid phosphatase by coupling with chondroitin sulfate), though never used to affect mechanical properties of enzyme-crosslinked hydrogels or matrices.
   IV. Enzymes can also be coupled to polysaccharides, such as dextran and starch derivatives such as hydroxyethyl starch. An example of this can be seen in example 13 where an enzyme was coupled to oxidized dextran.
3. Addition of one or more moieties to a single enzyme molecule through covalent modification(s). Often, but not always, the said moiety is smaller than the enzyme. An example for such a modification is PEGylation of the crosslinking enzyme, as extensively described below in multiple examples.
4. Other types of covalent binding. For example, by grafting biotin molecules on the surface of the enzyme (biotinylation) and immobilizing the biotinylated enzyme on avidin or streptavidin containing molecules or polymers. The carrier may be a non crosslinkable soluble polymer whose function is to capture the crosslinking enzyme before or during the crosslinking reaction. Alternatively, the capturing groups, e.g. avidin or streptavidin may be grafted on the crosslinkable polymer itself, resulting in gradual immobilization of the crosslinking enzyme during the crosslinking reaction on the crosslinkable polymer.
5. Non-covalent binding of the enzyme to a carrier or polymer. For example, electrostatic interactions between the enzyme and the carrier or polymer may provide a stable but non-covalent bond when the net charge of the enzyme has an opposite sign to the net charge of the carrier.

Technologies Related to Increasing the Size of Enzyme Molecules

Though increasing the size of enzymes has been previously disclosed on several occasions, it has never been considered in the context of forming and/or controlling the formation of enzyme crosslinked matrices or hydrogels. Application of size-increased enzymes in crosslinked matrices is entirely novel as the crosslinking reactivity of size increased enzymes in such matrices has not previously been characterized to any degree. Furthermore, the inventors of the present invention have surprisingly demonstrated that isolated enzyme activity of size-enhanced enzyme, as tested in a colorimetric enzyme activity assay, is distinctly different from the crosslinking activity of size-enhanced enzyme in hydrogel formation as indicated by gelation rate. For example, Example 5 describes a comparison of enzyme-catalyzed gelation rate to enzyme activity values measured using a colorimetric assay. PEGylation is described in this Example as a non-limiting, illustrative method for increasing enzyme size.

PEGylation is the covalent attachment of polyethylene glycol (PEG) molecules to enzyme molecules and is a preferred method of increasing enzyme molecule size. The operation of adding such one or more PEG molecules is known as PEGylation.

PEG is a desirable material for use in increasing enzyme size as it is bio-inert and has also demonstrated the ability to limit the immunogenic response to PEGylated implanted or injected molecules. Although it is not known whether PEGylation of enzymes as described herein also causes such immunogenic masking (limited immunogenic response), without wishing to be limited by a single hypothesis, it is possible that in fact PEGylation of the enzyme does limit the immunogenic response to the enzyme and also possibly, by extension, to the crosslinked matrix.

One method of accomplishing enzyme PEGylation is by reacting the enzyme with activated metoxyl PEG (mPEG) that react with amine groups on the enzyme (amine PEGylation). Non-limiting examples of activated mPEG include succinimidyl (NHS) esters of mPEG (mPEG-succinate-NHS, mPEG-glutarate, -NHS, mPEG-valerate-NHS, mPEG-carbonate-NHS, mPEG-carboxymethyl-NHS, mPEG-propionate-NHS, mPEG-carboxypentyl-NHS), mPEG-nitrophenylcarbonate, mPEG-propylaldehyde, mPEG-Tosylate, mPEG-carbonylimidazole, mPEG-isocyanate, mPEG-epoxide.

The activated mPEGs can be those that react with thiol groups on the enzymes (thiol PEGylation).

The activated PEGs may be monofunctional, heterobifunctional or homobifunctional.

The activated PEGs may be branched PEGs or multi-arm PEGs.

The size of the activated PEG may range from 1000 dalton to 40,000 dalton The molar ratio of the activated PEG to lysine groups on the enzyme is from 0.1:1 to 100:1 and preferably 0.5:1 to 10:1

Preferably, the pH of the PEGylation reaction is 7-9. More preferably the pH of the reaction is 7.5-8.5.

According to a preferred embodiment, the PEGylated enzyme may be further purified from non-reacted enzyme or in order to reduce the size range of the PEGylation products. The purification may be done using size-exclusion chromatography. Alternatively, or in addition, the purification may be done using ionic chromatography, such as SP-sephrose, Q-sepharose, SM-sepharose or DEAE-sepharose. Alternatively, or in addition, purification from non-reacted enzyme may also be done using dialysis, ultrafiltration or ammonium sulfate fractionation.

Various examples provided below describe the use of PEGylation of transglutaminases for control of cross-linked hydrogel formation. Example 1 describes PEGylation reaction of mTG with PEG-NHS (5 kD). The size and distribution of PEGylation products is dependent on the PEG to mTG ratio as well as the pH of the reaction.

Example 2 describes PEGylation reaction of mTG with PEG-NHS (5 kD). The size and distribution of PEGylation products is dependent on the duration and pH of the reaction.

Example 3 describes PEGylation reaction of mTG with PEG-NHS (2 kD). The size and distribution of PEGylation products is dependent on the PEG to mTG ratio.

Example 4 describes a TNBS assay for the determination of the PEGylation extent of various preparations of PEGylated mTG (5 kD PEG). The results suggest that the extent of PEGylation depends on the activated PEG:mTG ratio in the reaction.

Example 5 describes assays for the determination of activity of PEGylated mTG. The results suggest that PEGylated mTG retains most its activity towards small substrates, such as hydroxylamine and CBZ-Gln-Gly but loses a significant portion of its activity towards larger substrates such as gelatin.

Examples 6 and 7 describe SDS-PAGE analysis of elution profile of mTG and PEGylated mTG from crosslinked gelatin gels. The results suggest that the PEGylated mTG elutes from the gel more slowly and to a lesser extent than non-PEGylated mTG, possibly due to its larger size or hydrodynamic volume.

Example 8 describes the measurement of activity of mTG that has eluted from crosslinked gelatin gels. The results suggest that non-PEGylated mTG which is eluted from crosslinked gelatin gels retains most of its activity (86% of maximal calculated activity).

Example 9 describes the mechanical testing of gelatin gels crosslinked with PEGylated or non-PEGylated mTG. The results demonstrate that gelatin gels crosslinked with PEGylated mTG are stronger and considerably more flexible than gels cross-linked with non-PEGylated mTG.

Example 10 describes burst pressure testing of various gelatin sealant formulations. The results suggest that gelatin sealants made with PEGylated mTG demonstrate burst pressures results which are comparable to those of sealants made with non-PEGylated mTG.

Example 11 describes use of sealant for staple line reinforcement for in vivo porcine model.

Example 12 describes the effect of non-covalent binding of cross-linking enzyme to insoluble carrier.

Example 13 describes the effect of enzyme modification with oxidized dextran.

Example 14 demonstrates that modification of Horseradish Peroxidase (another crosslinking enzyme) by PEGylation can modify matrices formed by peroxidase crosslinking.

Example 15 demonstrates the effect of partial PEGylation of the cross-linking enzyme.

Example 16 demonstrates that free PEG (PEG molecule placed in solution with the crosslinking enzyme, but not covalently bound to the enzyme) has no effect on gelation.

Example 17 illustrates the effect of various mixtures of modified enzyme mixed with non-modified enzyme on gelation.

Example 18 demonstrates the effect of bi-functional PEG-enzyme bridges on gelation.

Example 19 relates to mass spectrometry analysis of PEGylated mTG (microbial transglutaminase).

Example 20 describes PEGylation of mTG at a fixed PEG to amine ratio with various concentrations of reactants, demonstrating the large effect of total reactant concentration on the extent of PEGylation.

Surprisingly it was found in these Examples that while PEGylation reduced the rate at which microbial transglutaminase (mTG) crosslinked gelatin, it did not decrease its activity in the hydroxamate assay, which is a gold standard activity assay for transglutaminases. These results contradict the background art teachings which indicated that size-enhanced enzyme might be undesirable for use in hydrogel formation as it might have significantly lower efficacy in causing hydrogel formation.

It should be noted that TGases (transglutaminases) are sometimes mentioned in the context of PEGylation in the background art; however, these references teach the use of TGase as a tool for enabling or enhancing site specific PEGylation of other proteins (rather than as a substrate for PEGylation) by catalyzing the transglutamination reaction of glutamyl residues on the said proteins with a primary amine group attached to the said PEG molecules. However, such background art does not teach or suggest PEGylation of TGases themselves in order to alter or control their crosslinking activity or to alter or control the mechanical properties of hydrogel matrices crosslinked by these enzymes.

Reduced Mobility of Crosslinking Enzyme by Coupling onto Crosslinked Matrix

In another embodiment of reducing enzyme mobility in a crosslinked matrix, the enzyme undergoes a binding reaction to the crosslinked matrix itself simultaneous to catalyzing the crosslinking reaction. As the enzyme moves through the polymer solution to crosslink the polymers in a matrix, it is gradually bound to the polymers themselves and thus immobilized in the matrix. For example, biotinylated enzyme can be mixed with a crosslinkable polymer component containing avidin or streptavidin coated polymer. U.S. Pat. No. 6,046,024 (Method of producing a fibrin monomer using a biotinylated enzyme and immobilized avidin) describes a method of capturing biotinylated thrombin from fibrinogen solution by adding avidin-modified agarose. Though in this case, the agarose was not soluble, it is possible to bind avidin or streptavidin to water soluble polymer as well as described by U.S. Pat. No. 5,026,785 (Avidin and streptavidin modified water-soluble polymers such as polyacrylamide, and the use thereof in the construction of soluble multivalent macromolecular conjugates). Biotinylation of transglutaminase and subsequent adsorption to avidin-treated surfaces has been shown to be feasible (Huang X L et al, *J. Agric. Food Chem.*, 1995, 43 (4), pp 895-901). Alternatively, the cross-linking enzyme may be covalently bound to avidin or streptavidin and the conjugate added to the crosslinking reaction which contains a biotinylated polymer. The biotinylated may be the crosslinkable polymer itself, e.g. gelatin, or a non-crosslinkable co-polymer such as dextran. Dextran-biotin conjugates of molecular weights of up to 500,000 dalton are available from commercial sources.

Reduced Mobility of Crosslinking Enzyme by Electrostatic Interactions in Crosslinked Matrix In another embodiment of the present invention, enzyme mobility is reduced through reversible binding based on electrostatic interactions between the enzyme and a polymer carrier in which the net charge of the enzyme has an opposite sign to the net charge of the carrier. The enzyme may be pre-incubated with the carrier and added to the crosslinking reaction or it may be bound to the carrier during the cross linking reaction. For example, if the crosslinking enzyme is positively charged at neutral pH it may be electrostatically bound to a negatively charged carrier, for example carboxymethyl cellulose (CMC). The enzyme may be incubated with CMC to allow binding and then the complex added to the crosslinking reaction, or the enzyme and CMC are added separately. In the latter case the enzyme will bind the CMC gradually during the crosslinking reaction. It is also possible to bind the enzyme to the crosslinkable polymer strands themselves during the crosslinking reaction, provided that the crosslinkable polymer bears an opposite sign charge relative to the crosslinking enzyme. Alternatively, the isoelectric point (pI) of the crosslinking enzyme can be shifted such that the enzyme acquires an opposite sign charge than that of the crosslinkable polymer or carrier.

In another embodiment, the crosslinking enzyme is modified in such a way that its isoelectric point (pI) is changed to result in a different net charge on the enzyme at a given pH. Examples of ways to reduce the pI of the enzyme are to modify the ε-amino group of lysines by processes such as but not limited to succinylation (with succinic anhydride), acetylation (with acetic anhydride), carbamylation (with cyanate), reductive alkylation (aldehydes) and treatment with maleic anhydride. This results in decrease in the positive net charge on the protein by up to one charge unit per modified amino acid (except for succinylation which decreases the positive net charge by up to two charge units) and decrease in the pI. Conversely, side chains containing carboxylic acids such as glutamic and aspartic acid may be modified in order to decrease the number of negative charges on the protein and as a result increase the pI. For example it is possible to treat the enzyme with EDC 1-Ethyl-3-[3-dimethylaminopropyl]carbodiimide) and ethylene diamine (EDA). EDC activates the carboxylic acid groups and an amide bond is formed between them and EDA. The result is an increase in the positive net charge of the protein and in the pI.

The release of proteins from hydrogels has been linked to electrostatic attraction and repulsion forces between the hydrogel polymer chains and the entrapped protein. It has been suggested that electrostatic repulsion forces increase the diffusion coefficient of the entrapped protein and conversely, electrostatic attraction forces decrease the diffusion coefficient in protein release experiments from recombinant gelatin matrix (Marc Sutter-Juergen Siepmann, Wim E. Hennink and Wim Jiskoot, Recombinant gelatin hydrogels for the sustained release of proteins, Journal of Controlled Release Volume 119, Issue 3, 22 Jun. 2007, Pages 301-312)

Changing the pI of the hydrogel polymer chain itself has been suggested as a way to control the release of proteins from that hydrogel. However, the background art involved manipulating electrostatic interactions between proteins entrapped within a hydrogel and the hydrogel chains are concerned with methods of controlling the release rate of the therapeutic proteins from the hydrogel, where the proteins are not themselves involved in the formation of the hydrogel. For at least some embodiments of the present invention, the electrostatic interactions are modified to improve the hydrogel mechanical properties, which may be related to mobility and diffusion coefficient of the enzyme in the hydrogel matrix that the enzyme is crosslinking.

Changing the pI of the entrapped crosslinking enzyme is therefore a novel approach to prevent over cross linking because the diffusion or mobility of the cross linking enzyme in the cross linkable matrix is severely restricted by modification of the pI of the entrapped enzyme rather than of the polymeric hydrogel.

Example 1: Effect of Reaction pH, and PEG: mTG Ratio on Size and Distribution of PEGylation Products Materials:
Activated PEG: mPEG-glutarate-NHS 5 kDa (SunBright ME-050GS, NOF corporation, Japan)
mTG:
Ajinimoto activa 10% further purified using SP-sepharose ion exchange chromatography. Activity: 604 units/ml in 0.2M sodium citrate pH 6 sodium citrate, Hepes, SDS and beta mercaptoethanol were from Sigma Aldrich. 30% Acrylamide/Bis 29:1 and Bio-Safe Coomassie G-250 stain were from Bio-Rad . . . . Molecular weight marker was Precision Plus Dual Color (Bio-Rad)

1 unit of mTG activity catalyzes the formation of 1.0 μmol of hydroxamate per min from N-CBZ-Gln-Gly and hydroxylamine at pH 6.0 at 37° C. A set of reactions was set up, each with a volume of 0.2 ml. All reactions contained 15 u/ml mTG, the appropriate reaction buffer—either 90 mM sodium citarte, pH 6 or 100 mM Hepes pH 7, and various amounts of activated PEG. The PEG-NHS reacts with primary amines in proteins, the epsilon-amine on side chains of lysine residues as well as the amino terminus of proteins. The ratios of PEG to lysine residues in the reaction mix is described in detail below, The reactions were incubated at 37° C. for 1:36 hr and then glycine was added to a final concentration of 110 mM in order to neutralize the excess of activated PEG molecules that have not reacted with the enzyme.

Samples from each reaction were denatured by heating at 90° C. in the presence of SDS and beta mercaptoethanol and were analyzed using SDS-PAGE (8% resolving gel, 4% stacking gel, Mini-Protean electrophoresis system, BioRad). To visualize the proteins the gel was stained with Bio-Safe Coomassie G-250 stain followed by destaining with water. The gel was scanned with CanoScan 8800F scanner and the image is shown in FIG. 1, showing the effect of reaction pH and activated PEG concentration on PEGylation products size and distribution. Lane assignments were as follows:
Lane 1: mTG (control)
Lane 2: Molecular size marker (from top to bottom: 250 kD, 150 kD, 100 kD, 75 kD, 50 kD, 37 kD, 25 kD)
Lane 3: 53.3 mg/ml activated PEG; 90 mM Na citrate pH 6; PEG to lysine ratio 9.15
Lane 4: 26.6 mg/ml activated PEG; 90 mM Na citrate pH 6; PEG to lysine ratio 4.59
Lane 5: 13.3 mg/ml activated PEG; 90 mM Na citrate pH 6; PEG to lysine ratio 2.30
Lane 6: 53.3 mg/ml activated PEG; 100 mM Hepes pH 7; PEG to lysine ratio 9.15

Lane 7: 26.6 mg/ml activated PEG; 100 mM Hepes pH 7; PEG to lysine ratio 4.59
Lane 8: 13.3 mg/ml activated PEG; 100 mM Hepes pH 7 PEG to lysine ratio 2.30

As can be seen from FIG. 1, larger amounts of PEG and increased pH resulted in enzyme having an increased apparent molecular weight on the gel.

Example 2: Effect of Reaction pH and Duration on Size and Distribution of PEGylation Products All reactions contained 15 u/ml mTG.
Materials:
Activated PEG:
mPEG-glutarate-NHS 5 kDa (SunBright ME-050GS, NOF corporation, Japan)
mTG:
Ajinimoto activa 10% further purified using SP-sepharose ion exchange chromatography. Activity: 604 units/ml in 0.2M sodium citrate pH 6
sodium citrate, Hepes, SDS and beta mercaptoethanol were from Sigma Aldrich.
30% Acrylamide/Bis 29:1 and Bio-Safe Coomassie G-250 stain were from Bio-Rad.
Molecular weight marker was Precision Plus Dual Color (Bio-Rad)
1 unit of mTG activity will catalyze the formation of 1.0 μmol of hydroxamate per min from N-CBZ-Gln-Gly and hydroxylamine at pH 6.0 at 37° C.

A set of reactions was set up, each with a volume of 0.2 ml, All reactions contained 15 u/ml mTG, the appropriate reaction buffer—either 100 mM Hepes, pH 7 or 100 mM Hepes pH 8, and 25 mg/ml PEG-NHS. The ratio of PEG to lysine residues in the reaction mix was 4.59.

The reactions were incubated at room temperature for 2 hr. Samples were taken at various time points as described below and glycine was added to a final concentration of 110 mM in order to neutralize the excess of activated PEG molecules that have not reacted with the enzyme.

Figure 2:
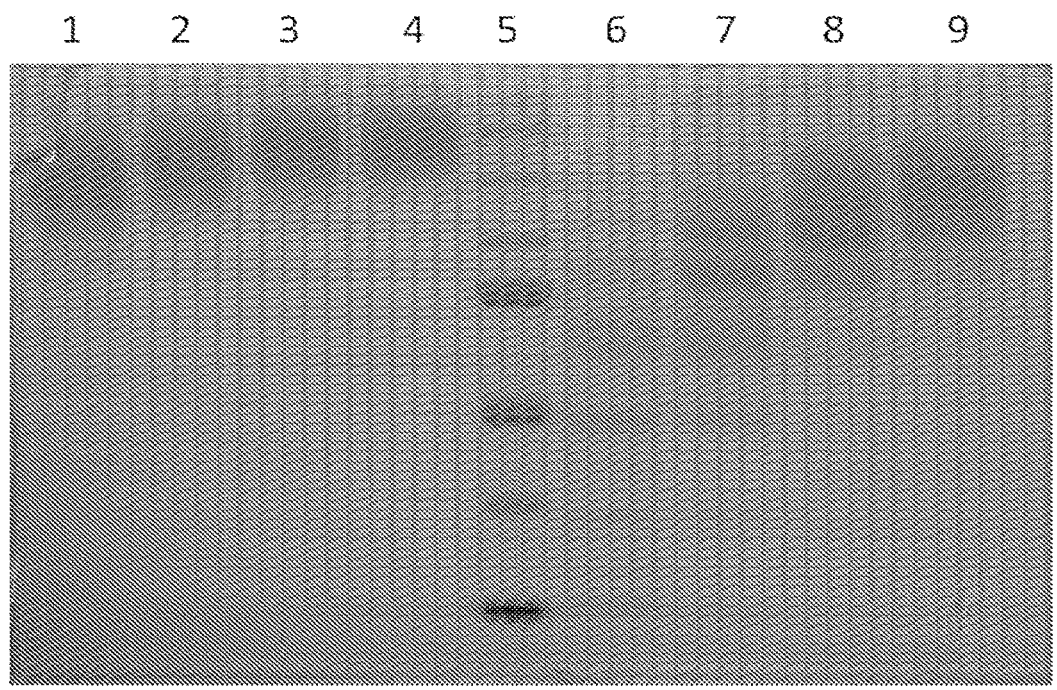
FIG. 2: Effect of reaction time and pH on size and distribution of PEGylation products.

Samples from each reaction were denatured by heating at 90° C. in the presence of SDS and beta mercaptoethanol and were analyzed using SDS-PAGE (8% resolving gel, 4% stacking gel, Mini-Protean electrophoresis system, BioRad). To visualize the proteins the gel was stained with Bio-Safe Coomassie G-250 stain followed by destaining with water. The gel was scanned with CanoScan 8800F scanner and the image is shown in FIG. 2, demonstrating the effect of reaction time and pH on size and distribution of PEGylation products. Lane assignments are as follows:
Lane 1: 25 mg/ml activated PEG; 100 mM Hepes pH 8; 15 min reaction time
Lane 2: 25 mg/ml activated PEG; 100 mM Hepes pH 8; 30 min reaction time
Lane 3: 25 mg/ml activated PEG; 100 mM Hepes pH 8; 60 min reaction time
Lane 4: 25 mg/ml activated PEG; 100 mM Hepes pH 8; 120 min reaction time
Lane 5: Molecular size marker (from top to bottom: 250 kD, 150 kD, 100 kD, 75 kD, 50 kD, 37 kD, 25 kD)
Lane 6: 25 mg/ml activated PEG; 100 mM Hepes pH 7; 15 min reaction time
Lane 7: 25 mg/ml activated PEG; 100 mM Hepes pH 7; 30 min reaction time
Lane 8: 25 mg/ml activated PEG; 100 mM Hepes pH 7; 60 min reaction time
Lane 9: 25 mg/ml activated PEG; 100 mM Hepes pH 7; 120 min reaction time As shown in FIG. 2, increased reaction time and increased pH resulted in enzyme having an increased apparent molecular weight on the gel.

Figure 3:
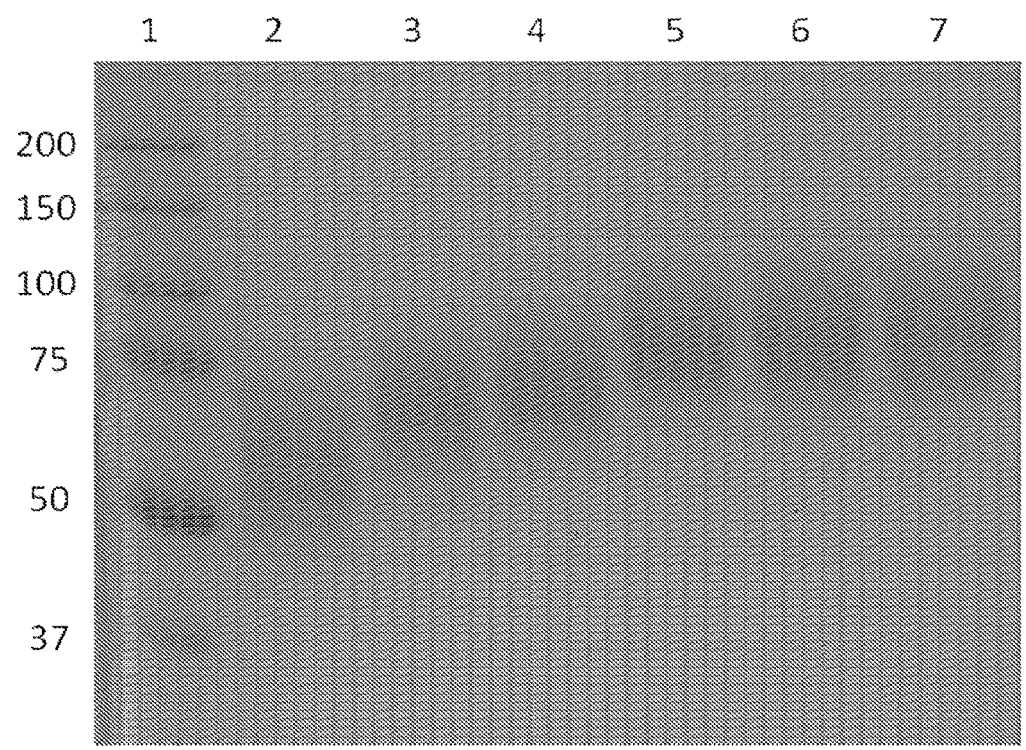
FIG. 3: SDS-analysis of PEGylated mTG using various concentrations of PEG-NHS (2 kD)

Example 3: PEGylation of mTG with PEG-NHS (2 kD): Effect of PEG: mTG Ratio on Size and Distribution of PEGylation Products Materials:
Activated PEG:
mPEG-glutarate-NHS 2 kDa (SunBright ME-020CS, NOF corporation, Japan)
mTG:
Ajinimoto activa 10% further purified using SP-sepharose ion exchange chromatography. Activity: 604 units/ml in 0.2M sodium citrate pH 6 sodium citrate, Hepes, SDS and beta mercaptoethanol were from Sigma Aldrich. 30% Acrylamide/Bis 29:1 and Bio-Safe Coomassie G-250 stain were from Bio-Rad.
Molecular weight marker was Precision Plus Dual Color (Bio-Rad).
1 unit of mTG activity will catalyze the formation of 1.0 μmol of hydroxamate per min from N-CBZ-Gln-Gly and hydroxylamine at pH 6.0 at 37° C. Reactions (200 μl) contained 15 u/ml mTG, 100 mM Hepes, pH 8 and various concentrations of PEG NHS (2 kD). The reactions were incubated at 37° C. for 2 hours, followed by addition of 10 μl 1.5 M glycine (71 mM final concentration) in order to neutralize the PEG-NHS molecules that have not reacted with the enzyme. Samples from each reaction were denatured by heating at 90° C. in the presence of SDS and beta mercaptoethanol and were analyzed using SDS-PAGE (8% resolving gel, 4% stacking gel, Mini-Protean electrophoresis system, BioRad). To visualize the proteins the gel was stained with Bio-Safe Coomassie G-250 stain followed by destaining with water. The gel was scanned with CanoScan 8800F scanner and the image is shown in FIG. 3, demonstrating SDS-analysis of PEGylated mTG using various concentrations of PEG-NHS (2 kD). Lane assignments are as follows:
Lane 1: Molecular size marker
Lane 2: 1.75 mg/ml PEG-NHS 2 kD; PEG to lysine ratio 0.74
Lane 3: 3.5 mg/ml; PEG-NHS 2 kD; PEG to lysine ratio 1.48
Lane 4: 7 mg/ml; PEG-NHS 2 kD; PEG to lysine ratio 2.97
Lane 5: 14 mg/ml; PEG-NHS 2 kD; PEG to lysine ratio 5.93
Lane 6: 28 mg/ml; PEG-NHS 2 kD; PEG to lysine ratio 11.86
Lane 7: 56 mg/ml; PEG-NHS 2 kD; PEG to lysine ratio 23.72

As shown in FIG. 3, increased amounts of PEG-NHS resulted in enzyme having an increased apparent molecular weight on the gel.

Example 4: TNBS Assay for Determining Extent of PEGylation

Materials:
Glycine and 5% TNBS solution (picrylsulfonic acid) were from Sigma Aldrich Sodium bicarbonate was from Frutarom (Israel)
Dilute TNBS solution was prepared by mixing 5% TNBS 1 in 500 in bicarbonate buffer (pH 8.5)
The spectrophotometer was Anthelie Advanced (Secomam)
For calibration curve, the following solutions of glycine were prepared in bicarbonate buffer (pH 8.5): 1 μg/ml, 2 μg/ml, 4 μg/ml, 8 μg/ml 0.5 ml of diluted TNBS solution was mixed with 1 ml of standard glycine solution or sample. The mixture was incubated at 37° C. for 2 hours. Next, 0.5 ml of 10% SDS solution and 0.25 ml of 1M HCL were added to stop the reaction. The solutions were transferred to a cuvette and the O.D. was read at 335 nm using a spectrophotometer.

The percentage of free $NH_2$ groups was determined for each PEGylated mTG based on the calibration curve set up for glycine.

% PEGylation=100−% of free $NH_2$

Calculated average MW of PEGylated mTG: 38,000+(% PEGylation:100×18×5000).

The results are shown in Table 1 below.

TABLE 1

| PEG-NHS (5 kD) conc. in reaction mg/ml | PEG to lysine ratio | % of free $NH_2$ groups | % PEGylation | Calculated average MW of PEGylated mTG |
|---|---|---|---|---|
| 3.5 | 0.59 | 38.8 | 61.2 | 93.08 kD |
| 7 | 1.19 | 28.9 | 71.1 | 101.99 kD |
| 14 | 2.37 | 20.8 | 79.2 | 109.28 kD |
| 28 | 4.75 | 13.9 | 86.1 | 115.49 kD |
| 56 | 9.49 | 10.9 | 89.1 | 118.19 kD |

The above table shows that increased PEGylation results in increased apparent (calculated) molecular weight of mTG; furthermore, the degree of PEGylation correlated with the reduction in the percentage of free lysine groups, indicating that PEGylation was occurring as expected on the lysine groups.

Example 5: Assays for Measuring the Activity of the PEGylated mTG

Materials:
Urea, Na citrate, Na Acetate and calcium chloride were from Sigma Aldrich Gelatin (Pig skin Type A 275 bloom) was from Gelita The PEGylation reaction (8 ml) contained 15 u/ml mTG, 100 mM HEPES (pH 7) and 14 mg/ml PEG-NHS (5 kD). The reaction conditions were similar to those in lane 8 in FIG. 1.

The reaction incubated at 37° C. for 1:50 hours, followed by addition of 0.4 ml 2.34 M glycine (100 mM final concentration) in order to neutralize the non-reacted activated PEG. After 15 minutes at room temperature the reaction mix was concentrated to 2 ml using Amicon Ultra-4 Centrifugal Filter Unit MWCO 30,000 (Millipore) and the reaction buffer changed to 0.2 M sodium citrate. The concentrated PEGylated mTG is referred to as 4×, while 2-fold and 4-fold dilutions of it in citrate buffer are referred to as 2× and 1×, respectively.

Activity Assay Using Gelatin as a Substrate
0.5 ml of mTG was mixed with 1 ml of gelatin formulation (25% gelatin, 3.8M urea, 0.15M $CaCl_2$, 0.1M Na acetate pH 6), incubated at 37° C. and the gelation time was recorded. By definition, gelation time is the time at which the liquid stops flowing when the reaction tube in inverted.

Activity Assay Using the Hydroxamate Assay
Reaction A 15 µl 1×non-PEGylated mTG (15 u/ml)+135 µl citrate buffer
Reaction B 15 µl 1×PEGylated mTG+135 µl citrate buffer
Reaction C 15 µl 2×PEGylated mTG+135 µl citrate buffer
Reaction D 15 µl 4×PEGylated mTG+135 µl citrate buffer 1 mL of reaction cocktail was added to each of reaction A-D and the mix was incubated at 37° C. for 10 minutes or 20 minutes. At each time point, 0.23 ml of the reaction was added to a tube with 0.5 mL TCA and 0.5 mL.

Hydroxamate reaction substrate cocktail (20 ml, pH 6):
240 mg CBZ-Glu-Gly (Sigma Aldrich)
139 mg hydroxylamine hydrochloride (Sigma Aldrich)
61.5 mg gluthatione reduced (Sigma Aldrich) 4 ml 0.2M Na citrate buffer pH 6
Water to 20 ml The results are shown in Table 2 below.

TABLE 2

| Sample tested | Pre-Pegylation enzyme activity | Gelation time with SLR | OD 525 in hydroxamate assay | |
|---|---|---|---|---|
| | | | 10 minutes | 20 minutes |
| 1X Non-PEGylated mTG | 15 u/ml | 4 min | 0.376 | 0.776 |
| 1X PEGylated mTG | 15 u/ml | 9 min | 0.358 | 0.722 |
| 2X PEGylated mTG | 30 u/ml | 4.5-5 min | 0.667 | 1.34 |
| 4X PEGylated mTG | 60 u/ml | 2.75 min | 1.263 | 2.152 |

Table 2 above shows that PEGylation of the transglutaminase caused an increase in gelation time at 1× PEGylation, but had little effect on the enzyme's activity in the hydroxamate assay (which occurs in free solution, without a hydrogel being formed). Increased amounts of PEGylation actually increased gelation time, presumably by reducing the mobility of the enzyme required for collision with substrate molecules within the forming crosslinked polymer network. Alternate explanations are that PEGylation is conferring a structural alteration to the enzyme's active site such that it cannot accommodate the substrate as efficiently as non-PEGylated enzyme or that the one or more PEG molecules inserted in the vicinity of the active site of the enzyme cause steric hindrance to an approaching substrate molecule. It is possible that the smaller size of substrate or the lack of crosslinked polymer network formation during the reaction in the hydroxamate assay are the reason for the lack of reduction of activity of PEGylated enzyme in this assay. All of these explanations are provided without wishing to be limited by a single hypothesis.

These results support the disparate effects of PEGylation upon formation of a hydrogel than on the enzyme's activity in solution. Without wishing to be limited by a single hypothesis, it is believed that these different effects occur as a result of the increased apparent size and/or perceived volume (other than caused by increased size) of the enzyme, which in turn provide beneficial effects for controlling formation of a hydrogel. In any case, according to at least some embodiments of the present invention, the differential effect of PEGylation enables crosslinking to be controlled during formation of a hydrogel.

Example 6: Elution Profile of PEGylated and Non-PEGylated mTG from Gels of Gelatin Materials:
Gelatin (Pig skin type A, 275 bloom) was from Gelita
30% Acrylamide/Bis 29:1 and Bio-Safe Coomassie G-250 stain were from Bio-Rad . . . . Molecular weight marker was Precision Plus Dual Color (Bio-Rad)

Figure 4:
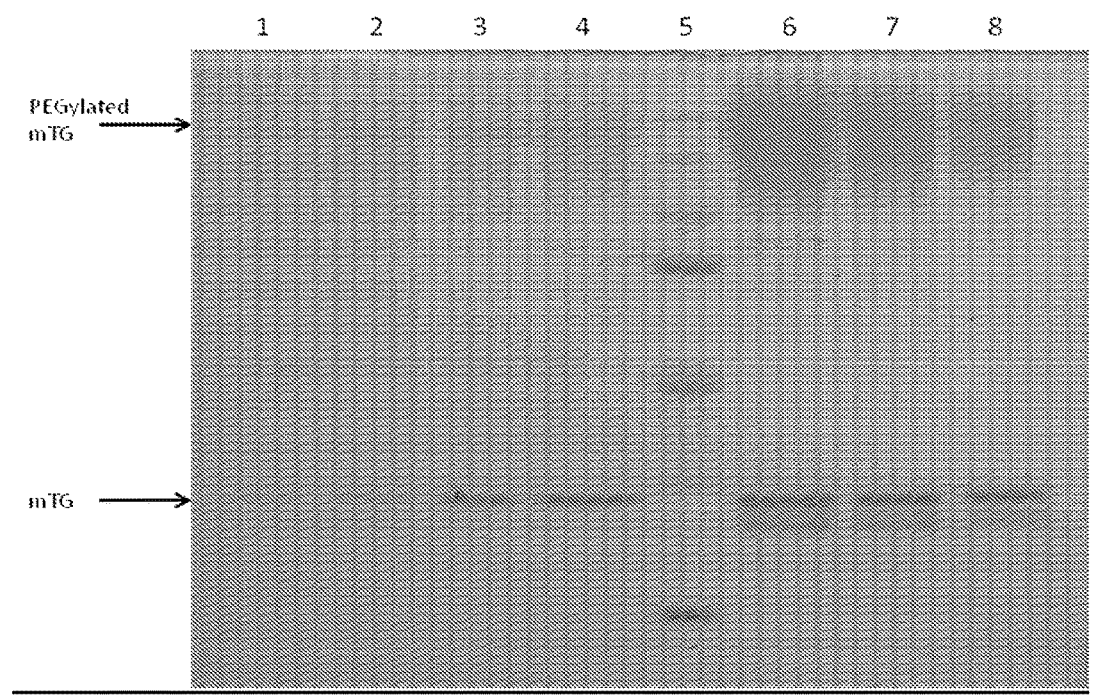
FIG. 4: Elution of mTG and PEGylated mTG from the same crosslinked gelatin gel.

A crosslinked gelatin gel was made by mixing 0.67 ml of an enzyme mix comprising of 1:1 mixture of PEGylated mTG (The reaction conditions were similar to those in lane 6 in FIG. 1) and 20 u/ml mTG with 1.33 ml of gelatin solution (25% gelatin, 3.8M urea, 0.15M $CaCl_2$, 0.1M Na acetate pH 6). The resulting gel was wrapped in saran wrap and incubated at 37° C. for 2 hours. Next, the gel was placed in a tube containing 10 ml saline and was incubated for 4 hours at 37° C. shaker incubator. Samples were taken every hour. Samples were concentrated using Amicon Ultra-4 Centrifugal Filter Unit MWCO 30,000 (Millipore), denatured by heating at 90° C. in the presence of SDS and beta mercaptoethanol and were analyzed using SDS-PAGE (8% resolving gel, 4% stacking gel, Mini-Protean electrophoresis system, BioRad). To visualize the proteins the gel was stained with Bio-Safe Coomassie G-250 stain followed by destaining with water. In order to quantitate the intensities of the bands in SDS-PAGE, the gel was scanned with CanoScan 8800F scanner and the resulting image, shown in FIG. 4, was analyzed using Quantity One software (Bio-Rad). The lane assignments are as follows: Lane 1: 10 μl sample taken at t=1 hour Lane 2: 20 μl sample taken at t=1 hour
Lane 3: 10 μl sample taken at t=4 hour
Lane 4: 20 μl sample taken at t=4 hour
Lane 5: Molecular size marker
Lane 6: 7 μl mTG+PEGylated mTG mix
Lane 7: 3 μl mTG+PEGylated mTG mix
Lane 8: 1.5 μl mTG+PEGylated mTG mixture FIG. 4 shows elution of mTG and PEGylated mTG from the same crosslinked gelatin gel. Table 3 shows the relative amounts of transglutaminase eluted from the gel.

TABLE 3

|  | % of mTG from total* |
| --- | --- |
| 1 hr elution | 21.6 |
| 4 hr elution | 37.3 |
| Enzyme mix | 14.9 |

*(Total = mTG + PEGylated mTG)

Example 7: Elution of Different Types of PEGylated mTG from Crosslinked Gelatin Gels Large Scale PEGylation of mTG with Different Concentrations of 2 kD or 5 kD PEG-NHS Activated PEG:
Reagents:
mPEG-glutaryl-NHS, MW 5000 (SunBright ME-050GS, NOF corporation, Japan)
mPEG-succinyl-NHS, MW 2000 (SunBright ME-020CS, NOF corporation, Japan)
mTG:
Ajinimoto active 10% further purified using SP-sepharose ion exchange chromatography.
30% Acrylamide/Bis 29:1 and Bio-Safe Coomassie G-250 stain were from Bio-Rad SDS and beta mercaptoethanol were from Sigma Aldrich The PEGylation reaction (32 ml) contained 15 u/ml mTG, 100 mM HEPES (pH 8) and various concentrations of PEG-NHS (2 kD or 5 kD). The reactions were incubated at room temperature for 2.5 hours, followed by addition of 2.2 ml 1.5 M glycine (97 mM final concentration) in order to neutralize the non-reacted activated PEG. After 15 minutes of further incubation at room temperature the reaction mix was concentrated down to 8 ml using Vivaspin 20 (Sartorius) while at the same time the reaction buffer was changed to 0.2 M Na citrate pH 6.

1 volume of different PEGylated mTGs (described above) were mixed with 2 volumes of gelatin formulation (25% gelatin, 3.8M urea, 0.15M $CaCl_2$, 0.1M Na acetate pH 6). The mixtures were poured into Teflon coated dog bone shaped molds. After gelation occurred, the gels were taken out of the molds, weighed, placed in a closed test tube to prevent drying and incubated at 37° C. for 3 hours. Next, exactly 5 ml of Na citrate pH 6 were added for each gram of gel, and the test tube was incubated at a 37° C. air shaker at 100 rpm. 0.5 ml samples were taken after 1 hr, 2 hr 3 hr and after further incubation for 18 hr at 30° C.

Samples from each timepoint were denatured by heating at 90° C. in the presence of SDS and beta mercaptoethanol and were analyzed using SDS-PAGE (8% resolving gel, 4% stacking gel, Mini-Protean electrophoresis system, BioRad). To visualize the proteins the gel was stained with Bio-Safe Coomassie G-250 stain followed by destaining with water. In order to quantitate the intensities of the bands in SDS-PAGE, the gel was scanned with CanoScan 8800F scanner and the resulting image, shown in FIG. 5, was analyzed using Quantity One software (Bio-Rad).

The maximal theoretical amount of enzyme that would have been released was loaded on the SDS-PAGE as well and was taken as 100% release. The actual elution samples were ran side by side and the intensities of the bands were calculated relative to the 100% release. In order to quantitate the intensities of the bands in SDS-PAGE, the gel was scanned with CanoScan 8800F scanner and the resulting image was analyzed using Quantity One software (Bio-Rad).

Figure 5:
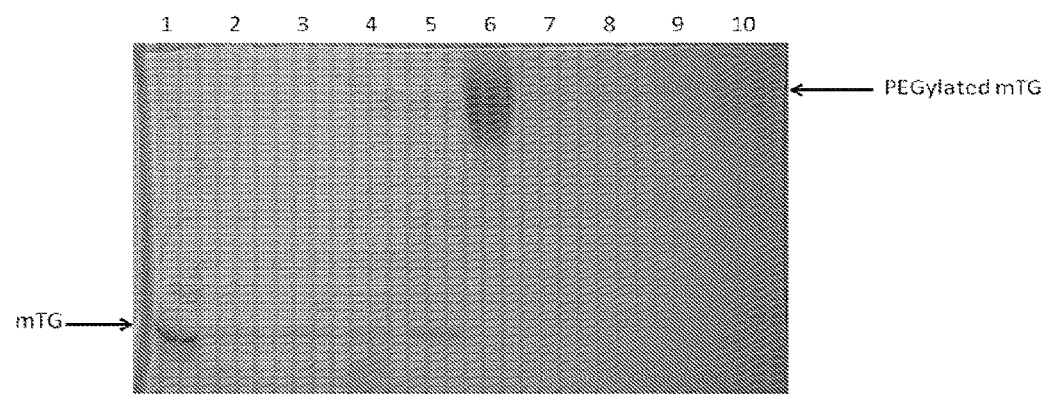
FIG. 5: Elution of mTG (left) and PEGylated mTG (right) from different crosslinked gelatin gels.

FIG. 5 shows elution of mTG (left) and PEGylated mTG (right) from different crosslinked gelatin gels. The lane assignments are given below.

Lane 1: mTG, 100% release reference
Lane 2: mTG released from crosslinked gelatin gel, 1 hr time-point
Lane 3: mTG released from crosslinked gelatin gel, 2 hr time-point
Lane 4: mTG released from crosslinked gelatin gel, 3 hr time-point
Lane 5: mTG released from crosslinked gelatin gel, 18 hr time-point
Lane 6: PEGylated mTG (7 mg/ml PEG-NHS, 5 kD)—100% release reference
Lane 7: PEGylated mTG (7 mg/ml PEG-NHS, 5 kD) released from gelatin gel, 1 hr time-point
Lane 8: PEGylated mTG (7 mg/ml PEG-NHS, 5 kD) released from gelatin gel, 2 hr time-point
Lane 9: PEGylated mTG (7 mg/ml PEG-NHS, 5 kD) released from gelatin gel, 3 hr time-point
Lane 10: PEGylated mTG (7 mg/ml PEG-NHS, 5 kD) released from gelatin gel, 18 hr time-point

TABLE 4

% elution from gelatin gels of different types of PEGylated mTG.

| Total release amounts are shown in Table 4 below. | % Elution from gel after 18 hr |
| --- | --- |
| Non-PEGylated mTG | 26.7 |
| PEGylated mTG (7 mg/ml PEG 5 kD) | 12.7 |
| PEGylated mTG (14 mg/ml PEG 5 kD) | 16.1 |
| PEGylated mTG (7 mg/ml PEG 2 kD) | 31.5 |
| PEGylated mTG (14 mg/ml PEG 2 kD) | 30.9 |

Example 8: Activity of mTG Eluted from Crosslinked Gels 9 ml of Non-PEGylated mTG which was eluted from gelatin gels for 18 hours (see Example 7) was concentrated to 0.47 ml using Vivaspin 20 (MWCO 30,000; Sartorious). The activity of the concentrated enzyme was determined using the hydroxamate assay as described in Example 5.

The measured activity was found to be 3.65 u/ml.

The calculated activity (based on initial activity in the gel of 5 u/ml and % release at 18 hr according to SDS-PAGE in FIG. 5 and its quantitation in Table 4 of 26.7%) is 4.24 u/ml.

Example 9: Mechanical Testing of Gelatin Gels Crosslinked with PEGylated or Non-PEGylated mTG Urea, Na citrate, Na Acetate and calcium chloride were from Sigma Aldrich.
Gelatin (Pig skin Type A 275 bloom) was from Gelita.
mTG was from Ajinimoto activa 10% further purified using SP-sepharose ion exchange chromatography. Activity: 604 units/ml in 0.2M sodium citrate pH 6.
PEGylated mTG (either 2 kD or 5 kD PEG-NHS) with various degrees of PEGylation was prepared as described in Example 7.

1 part of PEGylated mTG solution was mixed with 2 parts of gelatin solution (25% gelatin, 3.8M urea, 0.15M $CaCl_2$, 0.1M Na acetate pH 6). The mixture was poured into a Teflon-coated dog bone shaped mold. After gelation occurred, the gels were taken out of the molds, submerged in saline and incubated at 37° C. for 4 hours. The dimensions of the dogbone-shaped gel were then measured using a digital caliper. Control samples were made using 1 part of 15 u/ml of non-PEGylated mTG and 2 parts of gelatin solution. For both types of samples, the following testing protocol was followed:

The sample was clamped into a tensile testing system (Instron model 3343) such that the gel sample between the clamps was approximately 12 (width)×1.9 (thickness)×20 (length) mm. The precise dimensions of each sample were measured immediately prior to tensile testing and these measured values were used to calculate the material properties of the samples. Following clamping and measuring, tension was applied to each sample at a rate of 0.25 mm/s until a pre-load of 0.025 N was achieved. This was considered the 0% strain point. Following the preload, tensile strain was continuously applied to the sample at a rate of 0.5 mm/s until the sample failed by fracture.

The maximum strain and stress occurred at the fracture point such that the ultimate tensile strain and ultimate tensile stress were recorded at the point of fracture as Strain to break (%) and stress to break (kPa). Elastic modulus was calculated from the linear region between 10% and 30% strain for each sample.

Each type of crosslinked gelatin gel was tested with 5 repetitions and the average and standard deviations are summarized in Table 5.

TABLE 5

|  | Gelation time (min) | Young's Modulus (kPA) | Tensile stress at break (kPa) | Tensile strain at break (%) |
| --- | --- | --- | --- | --- |
| Control (15 u/ml) | 4.5 | 92.4 ± 7.4 | 42.5 ± 2.9 | 47.8 ± 4.9 |
| 7-2 | 4.5 | 72 ± 2.9 | 52 ± 13.6 | 81.9 ± 24.7 |
| 14-2 | 6.5 | 46 ± 4.6 | 36.6 ± 6.5 | 88.9 ± 19.8 |
| 7-5 | 3.5 | 90.4 ± 2.8 | 76.9 ± 11.6 | 98.9 ± 16.3 |
| 14-5 | 4.25 | 64.2 ± 5.6 | 77.7 ± 25.5 | 159.9 ± 52.6 |
| 28-5 | 5.5 | 47.6 ± 2.8 | 79.3 ± 16.5 | 221.7 ± 59.6 |

Table 5 shows the mechanical testing of various types of PEGylated mTG. The left most column refers to the conditions of PEGylation, given as A-B; the value of A as 7 refers to 7 mg/ml PEG, the value of A as 14 refers to 14 mg/ml PEG, and the value of A as 28 refers to 28 mg/ml PEG; the value of B as 2 refers to 2 kD PEG, while the value of B as 5 refers to 5 kD PEG. As shown, increased amounts of PEG result in increased gelation time and reduced Young's modulus; however, increased PEG size results in increased tensile strength and increased flexibility of the resultant gel.

Example 10: Performance of Sealant on Living Tissue Using the Burst Pressure Test Porcine small intestine tissues were cleaned of residual material and cut into 10 cm pieces. In each piece a 14 gauge needle puncture was made. The tissues were then be soaked in a saline solution and incubated at 37° C. Prior to applying the sealant material, which was prepared as described in Example 7, the tissue was flattened and the application site of each tissue was blotted using a gauze pad. Approximately 0.1-0.2 mL of tested sealant was applied on each application site using a 1 mL syringe. Within 5 min of the application the tissue was washed with saline and incubated at 37° C., for 4 hours. Each test group was examined in triplicates or more.

For the burst pressure test, the tissue were placed in the Perspex Box, one side tightly sealed (using a clamp) and the other connected to the pressure meter and hand pump (using a plastic restraint). The Perspex box was filled with saline so that tissue sample is totally submerged. Air was pumped, using the hand-pump at a constant rate (20 mL/min). Burst pressure was determined by the appearance of bubbles.

Figure 6:
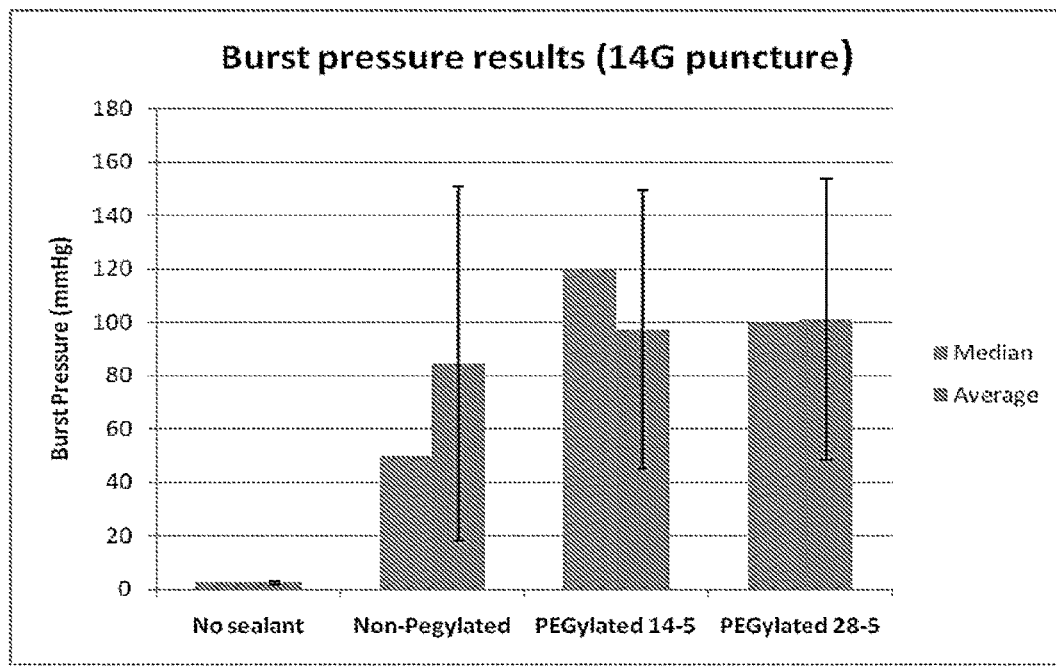
FIG. 6: Burst pressure values for gelatin sealant made with non-PEGylated mTG and 2 types of PEGylated mTG.

The results are shown in FIG. 6, indicating burst pressure values for gelatin sealant made with non-PEGylated mTG and 2 types of PEGylated mTG. As shown, the median results indicate an increase in burst pressure strength for both types of PEGylated mTG, although a somewhat greater effect is shown for the more moderately PEGylated enzyme.

Example 11: Use of Sealant for Staple Line Reinforcement for In Vivo Porcine Model A Covidien EEA circular surgical stapler was used to perform a circular anastomosis in the rectum of a pig.

Surgical sealant comprised of gelatin solution and PEGylated TG was prepared as in example 7, with 28 mg/ml 5 kDa PEG-NHS in a reaction volume of 72 ml. The reaction mix was concentrated using Viva-Spin 20 MWCO 30,000 (Sartorius) to 3 ml, such that the activity of the concentrated PEGylated enzyme was equivalent to 40 u/ml of non-PEGylated enzyme. 4 mL of sealant (comprised of 2.66 ml gelatin solution and 1.33 PEGylated enzyme solution) was applied evenly around the circumference of the rectal stapleline and left to cure for 4 minutes. The animal was then closed.

14 days post-surgery, the pig was sacrificed. The sealed anastomotic area was examined for gross pathology and the sealant was palpated to qualitatively assess its mechanical properties.
Result:
The sealant did not undergo significant degradation over the course of the 14 day implantation period. It remained strongly adhered to the staple line, maintaining 100% integrity over the length of the staple line. The sealant material was pliable and flexible, matching the shape and movement of the circular staple-line shape.
No inflammation or abdominal adhesions were noted in the area of the sealant or staple line. The anastomosis was fully healed with no signs of leakage. No strictures were observed in the rectum.

Example 12: Non-Covalent Binding of Cross-Linking Enzyme to Insoluble Carrier SP sepharose was bound to mTG (microbial transglutaminase) and a gel was made. Gelation occurred in 16-23 minutes with immobilized transglutaminase, while soluble enzyme caused gelation to occur in less than 6 minutes. Immobilization therefore increased the time required for gelation.
500 μl washed SP sepharose beads (GE Healthcare) were mixed with 2.7 ml 13.5 mg/ml of purified mTG with 11.55 ml 50 mM Na AC pH 5.5 (15 ml total).
The mixture was incubated in a shaker at room temperature for 20 minutes. The beads were then washed 3 times with 11.5 ml 50 mM NaAc pH 5.5, 3 minutes each wash. 70% of the protein was bound to the beads after the washing step. The beads were resuspended in 9.5 ml 50 mM NaAc pH 5.5 to a final volume of 10 ml. The mTG-loaded beads were mixed with 50 mM NaAc pH 5.5 in various compositions in a final volume of 600 μl as follows (in parenthesis the amount of bound mTG and the calculated theoretical mTG activity based on the measured activity of 1 mg unbound mTG—33 hydroxamate units):
  A: 292 μl beads+308 NaAc (1.244 mg/ml=41 u/ml)
  B: 400 μl beads+200 μl NaAc (1.704 mg/ml=56.2 u/ml))
  C: 5000 beads+100 μl NaAc (2.13 mg/ml=70.3 u/ml)
  D: 550 μl beads+50 μl NaAC (2.34 mg/ml=77.2 u/ml)
500 μl from each reaction A-D were mixed with 1 ml of 25% gelatin solution in sodium acetate buffer with 4.5M urea,) with syringe to syringe mixing. Gelation time was determined as the time in which the gelatin ceased to flow by visual inspection.
  Gelation Time:
  A: about 23 min
  B: about 21 min
  C: about 20 min
  D: about 16 min
  Control (unbound mTG 10 u/ml): 5.5 min
Gelation times with bound mTG were significantly slower compared to free enzyme. This suggests that binding of enzyme to a larger scaffold or insoluble carrier slows the mobility of the enzyme in a hydrogel matrix with the result that gelation, a sign of increased mechanical stiffness, is achieved at a later time point through cross-linking by bound enzyme as compared to free (unbound) enzyme. Thus, the enzyme binding resulted in modified mechanical properties of the hydrogel matrix.

Example 13: Enzyme Modification with Oxidized Dextran

This experiment demonstrates that modification of enzyme by binding large soluble molecule can result in modification of mechanical properties.
Methods
1 gram dextran was dissolved in 20 ml purified water. 1.3 gram sodium periodate was added and the reaction stirred at room temperature protected from light by aluminum foil for 80 minutes (9:50-11:10).
2 gram glycerol were added to quench the non-reacted periodate.
The reaction was dialyzed 3 times against 1 L PuW for 2:00 hr, with water change in between.

TABLE 6

Conjugation of mTG to oxidized dextran:

| | mTG:dextran ratio | mTG | Oxidized dextran | 1M phosphate pH 6.0 | Distilled water | NaBH$_4$CN 250 mg/ml in PuW |
|---|---|---|---|---|---|---|
| A | 1:4 | 0.75 ml (10 mg) | 0.8 ml (36.4 mg) | 0.4 | 1.05 | 0.1 ml (25 mg) |
| B | 1:1 | 0.75 ml (10 mg) | 0.2 ml (9.1 mg) | 0.4 | 1.65 | 0.1 ml (25 mg) |
| C | 4:1 | 0.75 ml (10 mg) | 0.05 ml (2.3 mg) | 0.4 | 1.8 | 0.1 ml (25 mg) |
| D | 10:1 | 0.75 ml (10 mg) | 0.02 ml (0.91 mg) | 0.4 | 1.83 | 0.1 ml (25 mg) |

Figure 7:
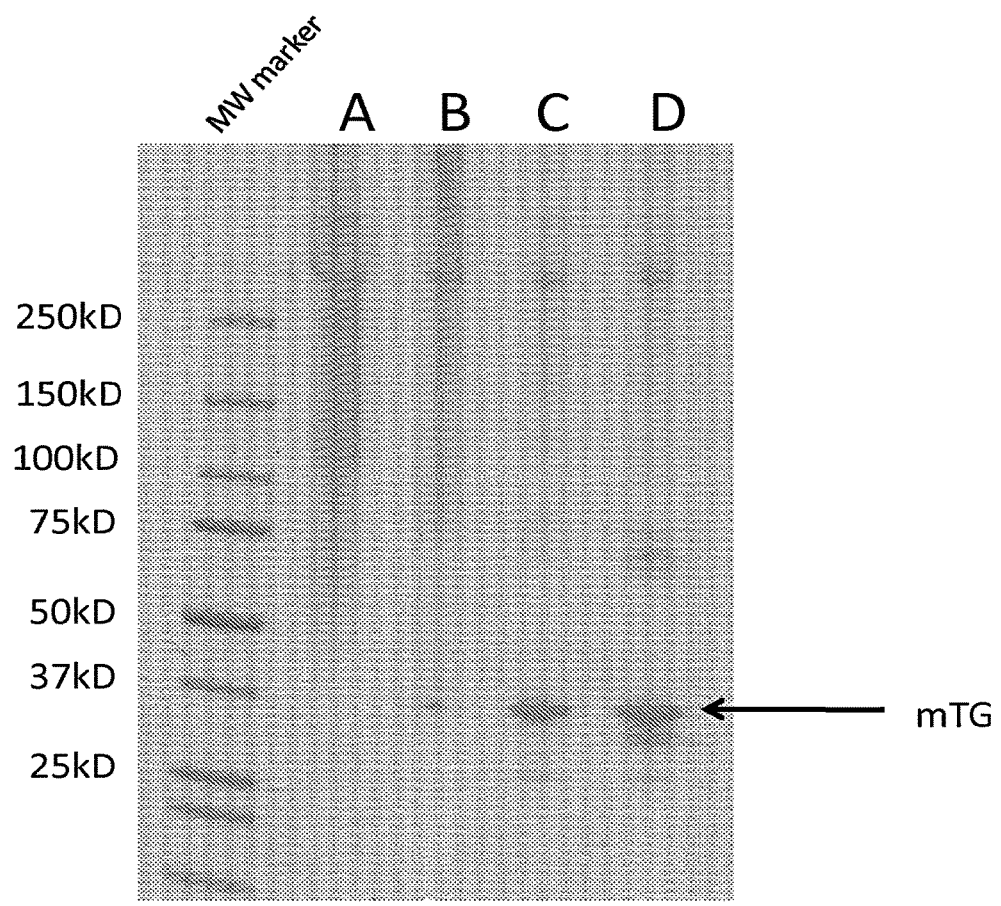
FIG. 7: SDS-PAGE analysis of conjugation products between mTG and dextran.

The reactions were incubated at room temperature overnight and then were purified by diafiltration using vivaspin 20 (Sartorius).
Results
FIG. 7 shows SDS-PAGE analysis of conjugation reactions A-D. The following amounts of dextran-conjugated mTG were loaded on a 4-15% Mini-Protean TGX gel (Bio-Rad): 4.35 μg (Reaction A), 4.38 μg (Reaction B), 1.98 μg (Reaction C) and 3 μg (Reaction D). The samples contained 0.1% SDS but no reducing agent and were heated at 85° C. for 10 minutes before loading. The gel was run at a constant voltage (200V) and the protein bands were visualized by staining with Bio-Safe Coomassie G-250 solution (Bio-Rad). The molecular weight marker was Precision Plus (Bio-Rad). The example shows that it is possible to immobilize a crosslinking enzyme, in this case mTG (microbial transglutaminase), on a soluble polymer. Furthermore, at higher dextran:mTG ratios, more molecules of free mTG are converted to high MW conjugates with dextran.

Example 14: Horseradish Peroxidase PEGylation

This experiment demonstrates that modification of Horseradish Peroxidase (another crosslinking enzyme) by PEGylation can modify matrices formed by peroxidase crosslinking. In another embodiment of the present invention, the crosslinking enzyme is horseradish peroxidase (HRP) and HRP is modified by attachment of PEG molecules to the HRP molecules in order to modify the mechanical properties of the gelatin hydrogel formed by HRP crosslinking.
Methods
Preparation of Phenol-Modified Gelatin (Gelatin-pH):
Two grams of high molecular weight gelatin Type A were dissolved in 100 ml 50 mM MES (2-(N-morpholino)ethanesulfonic acid; Sigma Aldrich) buffer pH 6. To this 2% w/w solution the following reagents were added: 0.984 gram tyramine (Sigma Aldrich). 0.218 gram NHS (N-Hydroxysuccinimide; Sigma Aldrich), 0.72 gram EDC (1-Ethyl-3-[3-dimethylaminopropyl]carbodiimide; Sigma Aldrich). The reaction was stirred at room temperature for 16 hours, and then dialyzed extensively against distilled water. The dialyzate was freeze dried and the resulting dry foam was dissolved in 0.1M phosphate buffer pH 6.0 to a final volume of 16 ml or 12.5% w/w gelatin.

PEGylation of HRP:

2 mg/ml HRP Type I (Sigma, St Louis, Mo.) were reacted with 60 mg/ml PEG-NHS 5 kD in 100 mM Hepes pH 8.0 for 2 hours, followed by addition of 110 mM glycine to quench the non-reacted PEG-NHS and 30 minutes further incubation. The PEGylated HRP was purified by extensive dialysis against 25 mM phosphate buffer pH 6.0.

HRP and PEGylated HRP Dependent Gelation of Gelatin-pH:

Gelatin component: 5 ml gelatin-Ph+0.5 ml 20 mM $H_2O_2$ mixed in a glass vial: 4.4 ml were transferred to syringe A. HRP/PEGylated HRP component: 1 ml 0.035 mg/ml HRPor PEGylated HRP in Syringe B. The gelatin and enzyme components were mixed by syringe to syringe transfer and then incubated at 37° C. while being inverted to determine gelation time.

After 20 minutes the gels were weighed, covered with 10 ml saline and incubated at 37° C. for 16 hours, after which the gels were weighed again to determine swelling ratio.

Results

Figure 8:
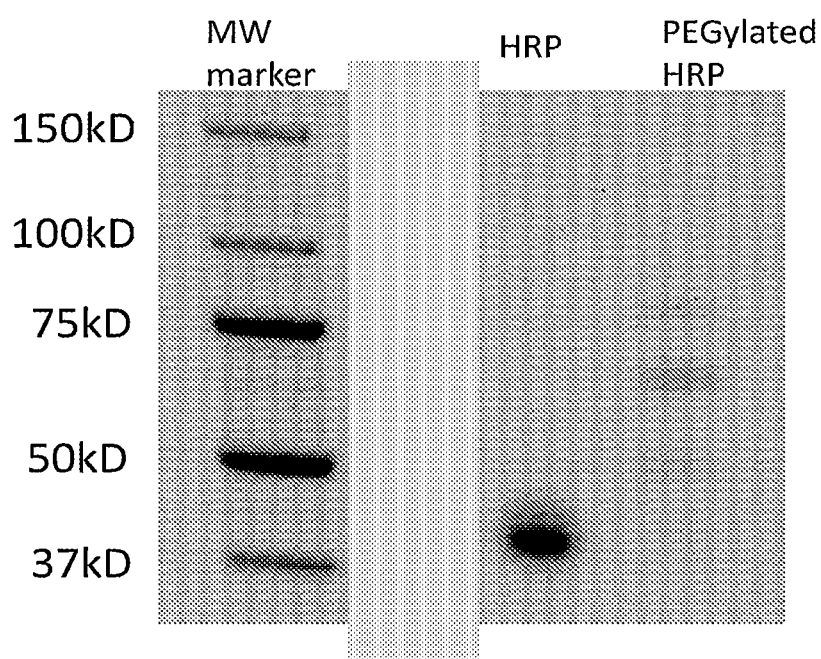
FIG. 8: SDS-PAGE analysis of PEGylation products of horseradish peroxidase (HRP)

After mixing, the gelatin and enzyme mixture formed a gel within 3 minutes. SDS-PAGE analysis for HRP and PEGylated HRP proteins can be seen in FIG. 8. HRP and PEGylated HRP (20 μg of each) were loaded on a 4-15% Mini-Protean TGX gel (Bio-Rad). The samples contained 0.1% SDS but no reducing agent and were heated at 85° C. for 10 minutes before loading. The gel was run at a constant voltage (200V) and the protein bands were visualized by staining with Bio-Safe Coomassie G-250 solution (Bio-Rad). The molecular weight marker was Precision Plus (Bio-Rad)

The measured swelling ratios are detailed below in Table 7:

TABLE 7

|  | Weight 20 minutes after gelation (A) | Weight after overnight at 37 deg C. (B) | % swelling (B − A)/ A × 100 |
| --- | --- | --- | --- |
| HRP gel 1 | 1.82 | 3.01 | 65.4 |
| HRP gel 2 | 1.33 | 2.29 | 72.2 |
| HRP gel 3 | 1.59 | 2.58 | 62.3 |
| PEGylated HRP gel 1 | 1.69 | 3.62 | 114.2 |
| PEGylated HRP gel 2 | 1.73 | 3.68 | 112.7 |

As can be seen in Table 7 above, the gels made with PEGylated HRP swelled to a larger extent than gels made with non-PEGylated HRP. This demonstrates that the mechanical properties of the gelatin hydrogels formed by the PEGylated (modified) HRP were significantly different than the mechanical properties of the hydrogels formed by the free (unmodified) HRP. Both types of gels were heat resistant and did not dissolve after 1 hour at 80 degC.

Example 15: Effect of Partial PEGylation

Cross-linking enzyme with pegylation to different degrees resulted in different degrees of mechanical properties. This example demonstrates how the mechanical properties of a enzymatically crosslinked hydrogel can be specifically controlled by modulating the hydrodynamic volume, in this case the degree of PEGylation, such that greater hydrodynamic volume (i.e. more PEGylation) results in a more elastic matrix and less hydrodynamic volume (i.e. less PEGylation results in a less elastic matrix. Naturally, the unmodified hydrodynamic volume (i.e. no PEGylation) results in the least elastic matrix. Instron data and SDS-Page gel data are described below with regard to these effects.

Methods

Three PEGylation reactions were performed side by side. The reactions were done at room temperature for 2.5 hr in 100 mM HEPES pH 8.0 using PEG-NHS 5K. Following the reaction, the unreacted excess PEG was neutralized with 110 mM glycine and incubation continued for 30 more minutes.

Reaction A and B had the same PEG:amine ratio but in A, both the mTG and the PEG were 3× more concentrated than in B. Reaction C is similar to A but the PEG:amine ratio was half the ratio in A. The results are shown in Table 8.

TABLE 8

|  | A | B | C |
| --- | --- | --- | --- |
| PEG conc (mg/ml) | 21.00 | 7.00 | 10.50 |
| PEG conc (mM) | 4.20 | 1.40 | 2.10 |
| mTG conc (mg/ml) | 5.96 | 2.00 | 5.95 |
| mTG amine conc (mM) | 3.15 | 1.05 | 3.14 |
| ratio PEG/amine | 1.33 | 1.33 | 0.67 |

Following the completion of these reactions, each resulting solution of PEGylated mTG solution was reacted with a 25% gelatin solution (in sodium acetate buffer with 4.5M urea) at a 1:2 ratio, mTG solution to gelatin solution, to form a gelatin hydrogel. The mTG activity levels of each PEGylated mTG solution were normalized such that the reaction time with the gelatin was identical for all groups. Following the formation of each hydrogel, it was cultured at 37° C. for 2 hours and then mechanically tested using a tensile testing system.

Figure 9:
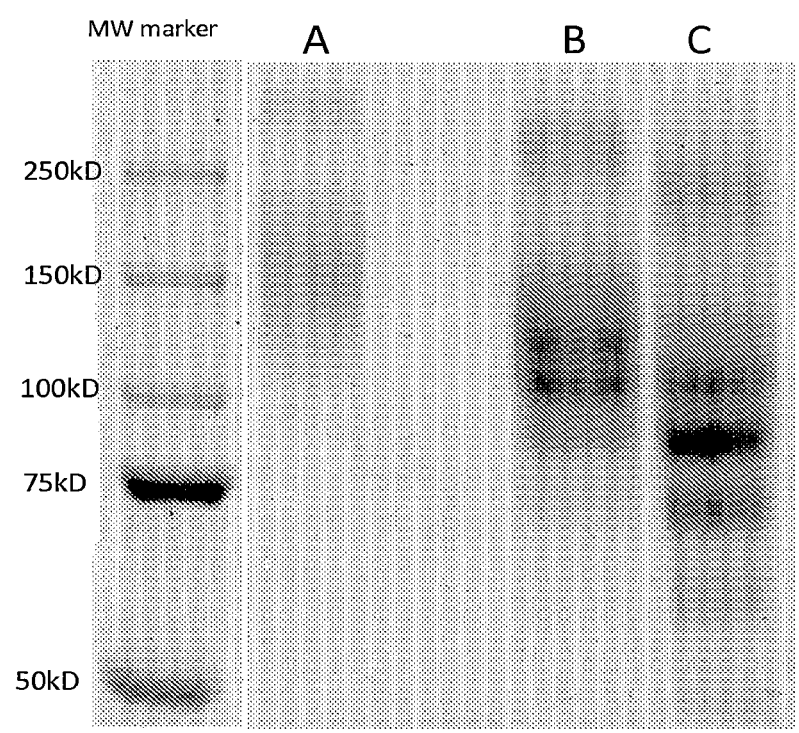
FIG. 9: SDS-PAGE analysis of PEGylation products of mTG, using various reactions conditions, the gel demonstrates various degrees of PEGylation.

Results are shown in FIG. 9, which is an image of SDS-PAGE analysis of PEGylated mTG. PEGylated mTG from reactions A, B and C (5 μg of each) were loaded on a 6% polyacrylamide gel and subjected to SDS-PAGE. The samples contained 0.1% SDS but no reducing agent and were heated at 85° C. for 10 minutes before loading. The gel was run at a constant voltage (200V) and the protein bands were visualized by staining with Bio-Safe Coomassie G-250 solution (Bio-Rad). The molecular weight marker was Precision Plus (Bio-Rad).

The SDS-PAGE profile shows how reactions A, B, and C resulted in mTG molecules bound with PEG molecules to different degrees such that many PEG molecules are bound to the mTG in A, fewer in B, and even fewer in C.

The varying degrees of PEGylation significantly affect the mechanical properties of the gelatin matrices as can be seen by the below results wherein the most PEGylated mTG, A, results in the most elastic (highest tensile strain at break) hydrogel and the non-PEGylated mTG results in the least elastic hydrogel, with the partially PEGylated mTG groups, B and C, falling out in between in correlation to each groups respective degree of PEGylation.

TABLE 9

|  | PEGylated mTG formula A | PEGylated mTG formula B | PEGylated mTG formula C | Control (non-PEGylated) |
| --- | --- | --- | --- | --- |
| Modulus (kPa) | 89.14 | 118.97 | 135.536 | 153.27 |
| Tensile stress at break (kPa) | 123.86 | 122.96 | 105.629 | 83.976 |

TABLE 9-continued

|  | PEGylated mTG formula A | PEGylated mTG formula B | PEGylated mTG formula C | Control (non-PEGylated) |
|---|---|---|---|---|
| Tensile strain at break (%) | 193.11 | 125.11 | 87.571 | 63.863 |

Example 16: Free PEG has No Effect on Gelation

As a control, Instron results of mechanical properties of gels were tested with and without free PEG. By "free" it is meant that the PEG molecule was placed in solution with the crosslinking enzyme, but was not covalently bound to the enzyme. The results showed that free PEG does not result in the mechanical property modifications brought about by covalent binding of PEG to the cross-linking enzyme (i.e. modification of the enzyme itself with PEG).

Methods 4 ml aliquots of gelatin solution (25% gelatin, 4.5M urea in sodium acetate buffer) with or without 20% PEG 6000 were each mixed with 2 ml aliquots of 15 u/ml mTG. 2 ml of each resulting solution was poured into dog-bone mold as described for Example 9. The resulting gel was taken out of the mold and incubated in saline at 37° C. for 2 hours, followed by tensile testing as described for Example 9.

Results

TABLE 10

|  | -PEG | +20% PEG 6000 |
|---|---|---|
| Modulus (kPa) | 73.72 | 55.03 |
| Tensile stress at break (kPa) | 41.74 | 30.13 |
| Tensile strain at break (%) | 57.7 | 57 |

The results of Table 10 demonstrate that the addition of free PEG, a plasticizer, had a minimal or no effect on enzyme crosslinked hydrogel matrix mechanical properties but that these mechanical property modifications are minor in comparison with the modifications achieved by increasing the hydrodynamic volume of the enzyme molecules through the attachment of PEG to the enzyme. In particular, the elasticity (strain to break) of the matrix was not improved at all by addition of free PEG, whereas PEGylation of the enzyme molecules results in a significant increase in matrix elasticity, as can be seen in several other examples.

Example 17: Mixed Modified/Non-Modified Cross-Linking Enzyme

Various mixtures of modified enzyme mixed with non-modified enzyme were tested. Different levels of modification of various mechanical properties can be obtained according to the specific mixture.

In another embodiment of the present invention, modified enzyme is used together with unmodified (free) enzyme in order to achieve mechanical modification of an enzyme-crosslinked matrix.

Methods 4 ml gelatin solution aliquots (25% gelatin, 4.5M urea, sodium acetate buffer) with or without 20% PEG 6000 were mixed with 2 ml 55 u/ml PEGylated mTG with or without additional non-PEGylated mTG and 2 ml of each resulting solution was poured into a dog-bone mold as described for Example 9. The resulting gel was taken out of the mold and incubated in saline at 37° C. for 24 hours, followed by tensile testing as described for Example 9.

Results

TABLE 11

|  | 55 u/ml PEGylated mTG | 55 u/ml PEGylated mTG + 5 u/ml free mTG | 55 u/ml PEGylated mTG + 10 u/ml free mTG |
|---|---|---|---|
| Modulus (kPa) | 73.5 | 134.88 | 163.06 |
| Tensile stress at break (kPa) | 101.17 | 89.64 | 87.66 |
| Tensile strain at break (%) | 170.51 | 74.73 | 57.65 |

The results of Table 11 indicate that mechanical properties of an enzyme crosslinked hydrogel can be modified both by using only modified enzyme and also, to a lesser degree, by using a mixture of modified enzyme with free enzyme.

Example 18: Bi-Functional PEG-Enzyme Bridges

This experiment demonstrated cross-linking of enzyme to itself through a bi-functional PEG bridge. For this example, two or more enzyme molecules can be bound to each other to increase the overall hydrodynamic volume of the enzyme aggregate. One way of accomplishing this is by using a bi-functional molecule that forms a bridge between enzyme molecules.

Methods mTG (15 u/ml, 0.5 mg/ml) was incubated with various concentrations of 10 kD bifunctional PEG-NHS in 100 mM Hepes pH8 at room temperature for 2 hours, followed by addition of 110 mM glycine for 30 more minutes to neutralize the excess non-reacted PEG. The specific conditions are shown in Table 12 below.

TABLE 12

| Reaction # | PEG concentration (mg/ml) | PEG:amine ratio |
|---|---|---|
| A | 0.78 | 0.296 |
| B | 1.56 | 0.59 |
| C | 3.125 | 1.18 |
| D | 6.25 | 2.36 |

Following the reaction, 5 μg of enzyme each reaction composition was loaded on a 7.5% polyacrylamide gel and subjected to SDS-PAGE analysis. The samples contained 0.1% SDS but no reducing agent and were heated at 85° C. for 10 minutes before loading. The gel was run at a constant voltage (200V) and the protein bands were visualized by staining with Bio-Safe Coomassie G-250 solution (Bio-Rad). The molecular weight marker was Precision Plus (Bio-Rad).

For mechanical property testing, 4 ml aliquots of gelatin solution (25% gelatin, 4.5M urea, sodium acetate buffer) were mixed with 2 ml aliquots of 15 u/ml either free mTG or PEGylated mTG (reaction C). 2 ml of the resulting solution were poured into dog-bone molds as described for Example 9. The resulting gel was taken out of the mold and incubated in saline at 37° C. for 24 hours, followed by tensile testing as described for Example 9.

Results

Figure 10:
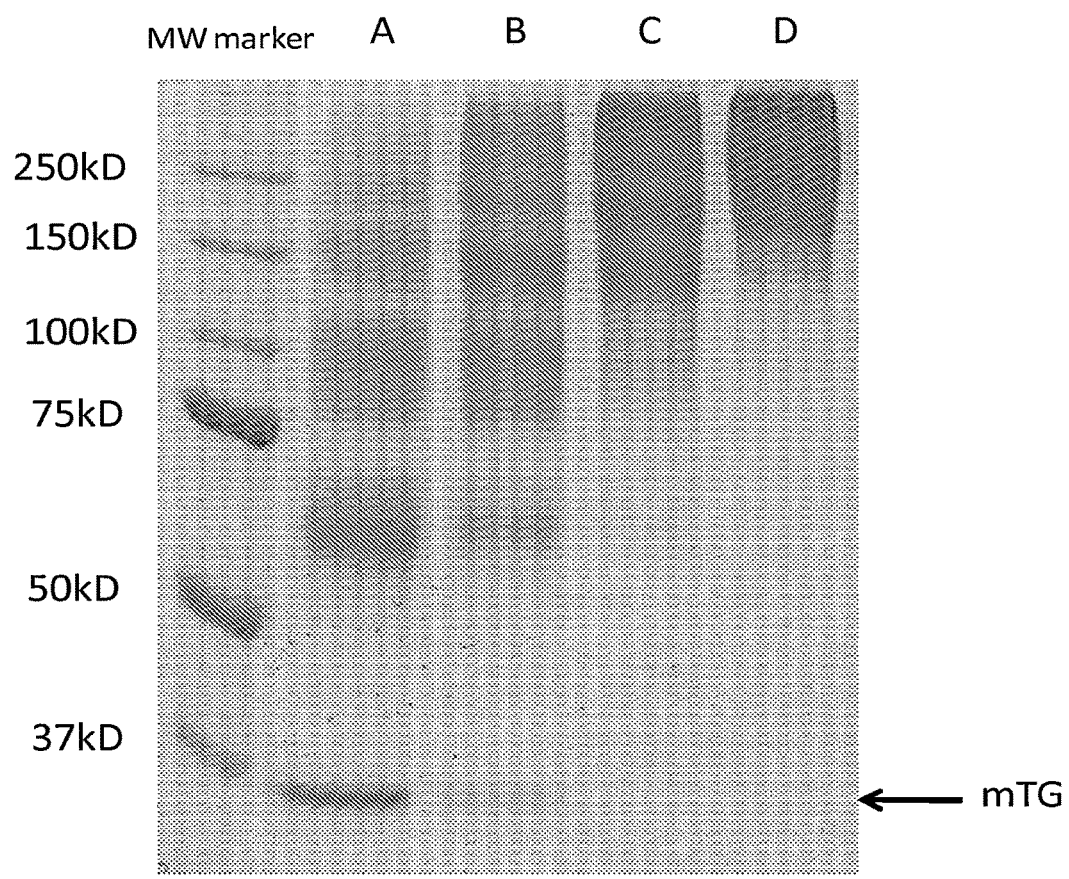
FIG. 10: SDS-PAGE analysis of PEGylation products of mTG, where the reactive PEG is a bifunctional 10 kD PEG-NHS.

The SDS-PAGE results of FIG. 10 shows that at relatively low PEG:mTG ratios, some of the mTG was converted to very high MW products, larger than PEGylated products obtained in reactions containing similar concentrations of monofunctional 5 kD PEG. This demonstrates that the high MW products consist of multimers of enzyme molecules crosslinked to each other by a bifunctional PEG bridge and demonstrate the efficacy of using bifunctional PEG to modify crosslinker enzyme molecules by binding them to each other.

The mechanical testing results below show that the binding of enzyme crosslinking molecules to each other results in significant modification to the gelatin hydrogels formed by crosslinking with these linked enzyme molecules, as compared with gelatin hydrogels formed by crosslinking with free enzyme molecules. The results are shown in Table 13.

TABLE 13

|  | 15 u/ml mTG | 15 u/ml mTG + bifunctional PEG-10K |
|---|---|---|
| Modulus (kPa) | 151.39 | 35.125 |
| Tensile stress at break (kPa) | 85.08 | 38.04 |
| Tensile strain at break (%) | 67.82 | 121.4 |

Example 19: Mass Spectrometry Analysis of PEGylated mTG

Figure 11:
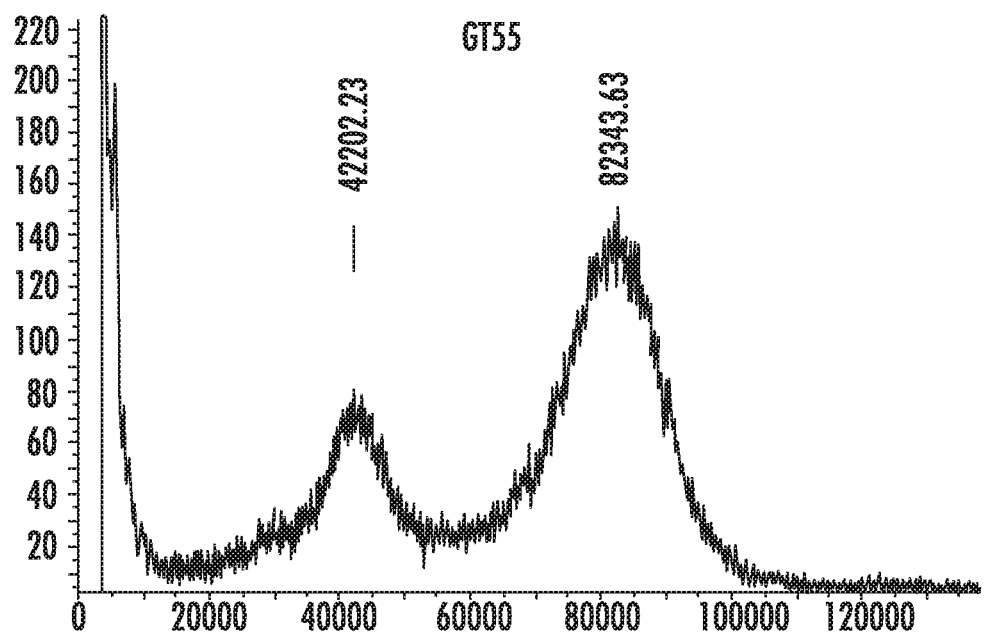
FIG. 11 shows mass to charge spectrum of a typical batch of PEGylated mTG acquired by MALDI-TOF mass spectrometer.

Three different batches of PEGylated mTG (microbial transglutaminase enzyme modified with PEG-NHS-5 kD) were analyzed by MALDI-TOF mass spectrometry. FIG. 11 shows the m/z spectrum of one of these batches.

Mass Spectrometry

Intact molecular mass measurement was performed on a Bruker Reflex III matrix-assisted laser desorption/ionization (MALDI) time-of-flight (TOF) mass spectrometer (Bruker, Bremen, Germany) equipped with delayed ion extraction, reflector and a 337 nm nitrogen laser. Each mass spectrum was generated from accumulated data of 200 laser shots. External calibration for proteins was achieved by using BSA and myoglobin proteins (Sigma, St Louis, Mo.).

Sample Preparation for MALDI-TOF MS—Dry Droplet Method.

2,5-Dihydroxybenzoic acid (DHB) 0.5 l of volume of matrix in 2:1 0.1% TriFluoroAcetic acid (TFA)-acetonitrile (ACN) and 0.5 l of sample solution in Formic acid/Isopropanol/H20 (1:3:2) were mixed on the target and allowed to air dry. After solvent evaporation the samples the samples were rewashed 1-3 times with 0.1% TFA.

TABLE 14

| PEGylation batch # | Average size main peak | Average size secondary peak | Calculated number of PEGs |
|---|---|---|---|
| 1 | 82343.63 | 42202.23 | 9.16 |
| 2 | 87430.04 | 44676.7 | 11.2 |
| 3 | 84543.16 | 44937.4 | 8.97 |

The results of Table 14 indicate that PEGylation of mTG crosslinking enzyme with 5 kDa PEG-NHS reagent results in the binding of multiple PEG molecules to each enzyme molecule.

Example 20: PEGylation of mTG at a Fixed PEG to Amine Ratio with Various Concentrations of Reactants This example demonstrates the large effect of total reactant concentration on the extent of PEGylation. When the ratio of PEG:amine was maintained at a fixed value, a correlation between the concentration of reactants (PEG and mTG) and the extent of PEGylation was demonstrated.

Methods

PEGylation of mTG with PEG-NHS-5 kD was carried out at room temperature in 100 mM Hepes pH 8.0 for 2.5 hours, followed by addition of 110 mM glycine to neutralize unreacted PEG-NHS. Following the reaction, 5 μg of enzyme each reaction composition was loaded on a 6.0% polyacrylamide gel and subjected to SDS-PAGE analysis. The samples contained 0.1% SDS but no reducing agent and were heated at 85° C. for 10 minutes before loading. The gel was run at a constant voltage (200V) and the protein bands were visualized by staining with Bio-Safe Coomassie G-250 solution (Bio-Rad). The molecular weight marker was Precision Plus (Bio-Rad).

Reactions were performed according to the below conditions (Table 15):

TABLE 15

|  | A | B | C | D | E |
|---|---|---|---|---|---|
| PEG conc. (mg/ml) | 1.75 | 3.50 | 7.00 | 14.00 | 21.00 |
| PEG conc. (mM) | 0.35 | 0.70 | 1.40 | 2.80 | 4.20 |
| mTG conc. (mg/ml) | 0.50 | 0.99 | 1.98 | 3.97 | 5.95 |
| mTG amine conc. (mM) | 0.26 | 0.52 | 1.05 | 2.09 | 3.14 |
| ratio PEG/amine | 1.34 | 1.34 | 1.34 | 1.34 | 1.34 |

Results

Figure 12:
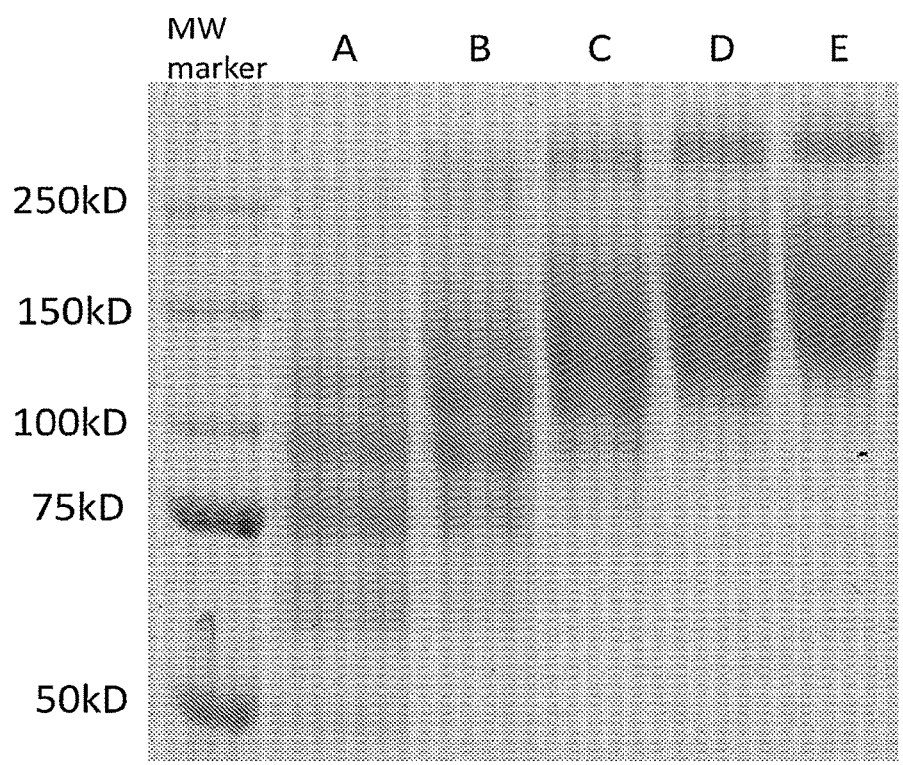
FIG. 12 shows SDS-PAGE analysis of PEGylation products of mTG where PEG reagent to amine ratio is kept constant but reactant concentration is varied.

The ensuing PEGylated mTG molecules can be seen in the SDS-PAGE lanes shown in FIG. 12. As can be seen, even when PEG:Amine ratio was kept fixed, the higher concentration of reactants resulted in product that was more PEGylated.

Although selected embodiments of the present invention have been shown and described individually, it is to be understood that any suitable aspects of the described embodiments may be combined, or indeed a plurality of embodiments may be combined.

In addition, although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cross-linked matrix, comprising a substrate polymer crosslinked by a modified enzyme molecule to form said crosslinked matrix, wherein the crosslinked matrix further comprises said modified enzyme molecule entrapped within the crosslinked matrix, said modified enzyme molecule modified by conjugating an enzyme molecule with a derivative of PEG (polyethylene glycol), thereby altering an effective volume of the modified enzyme molecule in the crosslinked matrix as the matrix is being formed through crosslinking of said polymer; wherein said effective volume is an effective hydrodynamic volume of said modified enzyme molecule inside the crosslinked matrix, such that altering said effective volume alters a diffusion coefficient of said modified enzyme molecule in comparison to said enzyme molecule before conjugation with said derivative of PEG; wherein said modified enzyme molecule has a reduced diffusion rate and a reduced cross-linking rate in comparison to said enzyme molecule before conjugation with said derivative of PEG, wherein an extent of said conjugation with said derivative of PEG is such that said reduced cross-linking rate is at least 10% of the enzyme cross-linking rate before conjugation of said enzyme molecule with said derivative of PEG.

2. The matrix of claim 1, comprising further modifying at least one epsilon-amino group of lysines on the enzyme molecule through a process selected from the group consisting of succinylation (with succinic anhydride), acetylation (with acetic anhydride), carbamylation (with cyanate), reductive alkylation (with an aldehyde) and maleylation (with maleic anhydride).

3. The matrix of claim 1, wherein said conjugating said enzyme molecule with said derivative of PEG modifies one or more side chains containing carboxylic acids of the enzyme to decrease the number of negative charges.

4. The matrix of claim 1, wherein said PEG derivative comprises activated PEG.

5. The matrix of claim 4, wherein said activated PEG comprises one or more of methoxy PEG (mPEG), mPEG-NHS, succinimidyl (NHS) esters of mPEG (mPEG-succinate-NHS), mPEG-glutarate-NHS, mPEG-valerate-NHS, mPEG-carbonate-NHS, mPEG-carboxymethyl-NHS, mPEG-propionate-NHS, mPEG-carboxypentyl-NHS), mPEG-nitrophenylcarbonate, mPEG-propylaldehyde, mPEG-Tosylate, mPEG-carbonylimidazole, mPEG-isocyanate, mPEG-epoxide.

6. The matrix of claim 5, wherein said activated PEG reacts with amine groups or thiol groups on said enzyme molecule.

7. The matrix of claim 4, wherein the molar ratio of said activated PEG to lysine residues of said enzyme molecule is in a range of from 0.5 to 25.

8. The matrix of claim 4, wherein said activated PEG is monofunctional, heterobifunctional, homobifunctional, or multifunctional.

9. The matrix of claim 8, wherein said activated PEG is branched PEG or multi-arm PEG.

10. The matrix of claim 8, wherein said activated PEG has a size ranging from 1000 dalton to 40,000 dalton.

11. The matrix of claim 1, wherein said modified enzyme molecule comprises a plurality of modified enzyme molecules cross-linked together to form an aggregate of a plurality of cross-linked enzyme molecules.

12. The matrix of claim 1, wherein at least one property of the crosslinked matrix formed by cross-linking said substrate polymer with said modified enzyme molecule is altered in comparison to cross-linking of said substrate polymer with said enzyme molecule before conjugation with said derivative of PEG, wherein said at least one property is selected from the group consisting of tensile strength, stiffness, extent of crosslinking of said substrate polymer, viscosity, elasticity, flexibility, strain to break, stress to break, Poisson's ratio, swelling capacity and Young's modulus, or a combination thereof.

13. The matrix of claim 1, wherein a ratio of PEG:amine on said modified enzyme molecule determines mobility of said modified enzyme molecule in, or diffusion from, the matrix.

14. The matrix of claim 1, wherein a ratio of PEG:amine on said modified enzyme molecule determines one or more matrix mechanical properties.

15. The matrix of claim 1, wherein said modified enzyme molecule shows a greater differential of crosslinking rate in crosslinked substrate polymer than in solution as compared to enzyme molecule before said enzyme molecule before conjugation with said derivative of PEG.

16. The matrix of claim 1, wherein said substrate polymer comprises a substrate polymer selected from the group consisting of a naturally cross-linkable polymer, a partially denatured polymer that is cross-linkable by said modified enzyme molecule and a modified polymer comprising a functional group or a peptide that is cross-linkable by said modified enzyme molecule.

17. The matrix of claim 16, wherein said substrate polymer comprises gelatin, collagen, casein or albumin, or a modified polymer, and wherein said modified enzyme molecule comprises a modified transglutaminase and/or a modified oxidative enzyme.

18. The matrix of claim 17, wherein said modified polymer is modified to permit crosslinking by said modified microbial transglutaminase.

19. The matrix of claim 17, wherein said substrate polymer comprises gelatin selected from the group consisting of gelatin obtained by partial hydrolysis of animal tissue or collagen obtained from animal tissue, wherein said animal tissue is selected from the group consisting of animal skin, connective tissue, antlers, horns, bones, fish scales, and a recombinant gelatin produced using bacterial, yeast, animal, insect, or plant systems or any type of cell culture, or any combination thereof.

20. The matrix of claim 19, wherein said gelatin is of mammalian or fish origin.

21. The matrix of claim 20, wherein said gelatin is of type A (Acid Treated) or of type B (Alkaline Treated).

22. The matrix of claim 21, wherein said gelatin is of 250-300 bloom.

23. The matrix of claim 22, wherein said gelatin has an average molecular weight of 75-150 kda.

24. The matrix of claim 19, wherein said modified transglutaminase comprises modified microbial transglutaminase.

25. The matrix of claim 19, wherein said modified oxidative enzyme comprises one or more of tyrosinase, laccase, or peroxidase.

26. The matrix of claim 25, wherein said matrix further comprises a carbohydrate comprising a phenolic acid for being cross-linked by said modified oxidative enzyme as said substrate polymer.

27. The matrix of claim 26, wherein said carbohydrate comprises one or more of arabinoxylan and pectin.

28. The matrix of claim 1, wherein said modified enzyme molecule is masked from an immune system of a host animal receiving the matrix n comparison to said enzyme molecule before conjugation with said derivative of PEG.

29. The matrix of claim 28, wherein said host animal is human.

30. A method for sealing a tissue against leakage of a body fluid, comprising applying a matrix of claim 1 to the tissue.

31. The method of claim 30, wherein said body fluid comprises blood, such that said matrix is a hemostatic agent.

32. A hemostatic agent or surgical sealant, comprising a matrix of claim 1.

33. A composition for sealing a wound, comprising a matrix of claim 1.

34. A composition for a vehicle for localized drug delivery, comprising a matrix of claim 1.

35. A composition for tissue engineering, comprising a matrix of claim 1, adapted as an injectable scaffold.

* * * * *